(12) United States Patent
Kraft et al.

(10) Patent No.: US 9,474,911 B2
(45) Date of Patent: Oct. 25, 2016

(54) DELIVERY OF LARGE MOLECULAR WEIGHT BIOLOGICALLY ACTIVE SUBSTANCES

(75) Inventors: Edward R. Kraft, Galveston, TX (US); Gabriela Kulp, Santa Fe, TX (US)

(73) Assignee: PhotoKinetix Holdings Inc., Galveston, TX (US)

( * ) Notice: Subject to any disclaimer, the term of this patent is extended or adjusted under 35 U.S.C. 154(b) by 137 days.

(21) Appl. No.: 14/008,047

(22) PCT Filed: May 20, 2011

(86) PCT No.: PCT/EP2011/058293
§ 371 (c)(1),
(2), (4) Date: Jan. 6, 2014

(87) PCT Pub. No.: WO2012/130336
PCT Pub. Date: Oct. 4, 2012

(65) Prior Publication Data
US 2014/0128798 A1    May 8, 2014

Related U.S. Application Data

(60) Provisional application No. 61/468,755, filed on Mar. 29, 2011.

(51) Int. Cl.
| | | |
|---|---|---|
| A61K 9/00 | (2006.01) |
| A61N 5/06 | (2006.01) |
| A61K 8/02 | (2006.01) |
| A61K 8/97 | (2006.01) |
| A61K 45/06 | (2006.01) |
| A61K 8/34 | (2006.01) |
| A61K 8/64 | (2006.01) |
| A61Q 19/00 | (2006.01) |
| A61K 41/00 | (2006.01) |
| A61K 9/70 | (2006.01) |

(52) U.S. Cl.
CPC .......... *A61N 5/0613* (2013.01); *A61K 8/0208* (2013.01); *A61K 8/345* (2013.01); *A61K 8/645* (2013.01); *A61K 8/975* (2013.01); *A61K 9/7046* (2013.01); *A61K 41/0019* (2013.01); *A61K 45/06* (2013.01); *A61Q 19/00* (2013.01); *A61N 5/062* (2013.01); *A61N 2005/065* (2013.01)

(58) Field of Classification Search
None
See application file for complete search history.

(56) References Cited

U.S. PATENT DOCUMENTS

| | | | |
|---|---|---|---|
| 7,458,982 B2 | 12/2008 | Kraft et al. | |
| 7,854,753 B2 | 12/2010 | Kraft et al. | |
| 2004/0131687 A1* | 7/2004 | Kraft .................... | A61K 9/0014 424/486 |
| 2004/0265268 A1* | 12/2004 | Jain ......................... | A61K 8/64 424/85.1 |
| 2009/0186072 A1 | 7/2009 | Yanaki | |

FOREIGN PATENT DOCUMENTS

| | | |
|---|---|---|
| WO | WO-2009/124763 A2 | 10/2009 |
| WO | WO-2009/139900 A1 | 11/2009 |
| WO | WO-2011/044589 A2 | 4/2011 |

* cited by examiner

*Primary Examiner* — Jeanette Lieb
(74) *Attorney, Agent, or Firm* — McCarter & English, LLP; Yu Lu

(57) ABSTRACT

The invention relates generally to intradermal, transdermal, and/or transmembrane delivery of biologically active substances in the epidermis and/or through the skin, sub-dermal tissues, blood vessels and cellular membranes without causing damage to the cellular surface, tissue or membrane. The biologically active substances may have a molecular weight no less than about 5.8 kDa to about 2,500 kDa, such as Hyaluronic Acid (HA). The biologically active substances may be deposited in a dermal patch containing a red algae polysaccharide-based matrix, wherein the red algae polysaccharide is an extract of *Chondrus crispus* at 2% by weight of the dermal patch. The invention provides systems and methods for enhanced intradermal, transdermal, and/or transmembrane delivery of such biologically active substances using pulsed incoherent light. The invention further provides a device for the application of the pulsed incoherent light to cellular surfaces and membranes using those compositions and methods.

27 Claims, 15 Drawing Sheets

FIG. 10A

Botulinum Toxin A
Passive vs Photokinetic Transdermal Permeation
2 U/ml Donor Concentration $* p<0.001$ vs Ctrl Y-axis: Units/ cm²/ 24 Hour X-axis categories: Ctrl | 405 nm 24 cps | 405 nm 100 cps | 450 nm 24 cps | 450 nm 100 cps Mean ± SEM

FIG. 10B

**Botulinum Toxin A
Skin Depostion**
2 U/ml Donor Concentration $* p<0.05$ vs Ctrl Y-axis: Units/ mg Protein/ mg Skin (0.1 to 1.0)

X-axis categories: Ctrl, 405 nm 24 cps, 405 nm 100 cps, 450 nm 24 cps, 450 nm 100 cps Mean ± SEM

```
                              SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Tyr Gly Gly Phe Met
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Tyr Gly Gly Phe Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 3

Asp Arg Val Tyr Ile His Pro Phe
1               5
```

DELIVERY OF LARGE MOLECULAR WEIGHT BIOLOGICALLY ACTIVE SUBSTANCES

REFERENCE TO RELATED APPLICATIONS

This application is a U.S. national stage application filed under 35 U.S.C. §371, of International Application No. PCT/EP2011/058293, filed on May 20, 2011, which claims the benefit of the filing date, under 35 U.S.C. §119(e), of U.S. Provisional Application No. 61/468,755, filed on Mar. 29, 2011, the entire contents of each of which are incorporated herein by reference.

BACKGROUND OF THE INVENTION

This invention relates to photokinetic delivery of biologically active substances from an outer mammalian skin surface. Depending on specific needs, the biological substance can be delivered intradermally (e.g., substantially locally to the epidermis level by, for example, predicting the intradermal drug deposition over time and modulating that deposition through turning off the light and thus the photokinetic process), for example, in cosmetic uses in the skin, or be delivered transdermally (e.g., to an underlying tissue or blood vessel), for example, in pharmaceutical uses. The biological substance can also be delivered from an extracellular environment to intracellular environment (transmembrane).

More particularly, the invention provides compositions for enhanced intradermal, transdermal, or transmembrane delivery of biologically active substances using pulsed incoherent light. In addition, the invention provides methods and devices for application of pulsed incoherent light to an area of mammalian skin or membrane for safe and efficient intradermal, transdermal, or transmembrane delivery of biologically active substances into or through the skin surface or cellular membrane.

For example, in the pharmaceutical field, therapeutic agents or biologically active substances can be administered to vital tissues and organs in a mammal by a plethora of delivery routes including, for example, oral, nasal, aural, anal, dermal, ocular, pulmonary, intravenous, intramuscular, intra-arterial, intraperitoneal, mucosal, sublingual, subcutaneous, and intracranial routes. In the last decade, transdermal delivery of biologically active substances has gained momentum due to the advantages it provides over those of conventional dosage routes, such as oral and intravenous administration. For example, biologically active substances or drugs delivered transdermally avoids deactivation caused by pH and digestive enzymes upon passage of the active substance through the gastrointestinal (GI) tract. In addition, other advantages of transdermal delivery include, but are not limited to, single application regimens or decreased dosages, increased patient compliance, high percentage of drug reaching the systemic circulation, sustained activity for drugs having short half-lives, controlled release of drugs (no "burst effect"), ability to quickly terminate drug dosing causing adverse effects and administration of drugs without hypodermic injection.

The success of transdermal delivery in a mammal relies on the ability of biologically active substances to penetrate the outer layer of the epidermis known as the stratum corneum. The stratum corneum is comprised mainly of about 10 to about 20 layers of flattened dead cells (corneocytes) filled with keratin. Lipids, such as free fatty acids, cholesterol, and ceramides, connect the regions between the keratinized cells, forming a brick and mortar-like structure. In mammals, this structure primarily serves as a barrier to chemicals and biological agents, including bacteria, fungus, and viruses.

The penetration of biologically active substances through the stratum corneum occurs by either passive or active transport mechanisms. Passive delivery or diffusion relies on a concentration gradient between the drug at the outer surface and the inner surface of the skin. The diffusion rate is proportional to the gradient and is modulated by a molecule's size, hydrophobicity, hydrophilicity and other physiochemical properties as well as the area of the absorptive surface. Examples of passive delivery systems include transdermal patches for controlled delivery of, for example, nitroglycerine (angina), scopolamine (motion sickness), fentanyl (pain control), nicotine (smoking cessation), estrogen (hormone replacement therapy), testosterone (male hypogonadism), clonidine (hypertension), and lidocaine (topical anesthesia). The controlled delivery of these drugs can include the use of polymer matrices, reservoirs containing drugs with rate-controlling membranes and drug-in-adhesive systems.

In contrast, active delivery relies on ionization of the drug or other pharmacologically active substances and on means for propelling the charged ions through the skin. The rate of active transport varies with the method used to increase movement and propulsion of molecules, but typically this transport provides a faster delivery of biologically active substances than that of passive diffusion. Active transport delivery systems include methods such as iontophoresis, sonophoresis, thermal microporation, and microporation using mechanical means, such as microinjection using microneedles or needleless injection.

Iontophoresis is a technique used to guide one or more therapeutic ions in solution into the tissues and blood vessels of the body by means of a galvanic or direct electrical current supplied to wires that are connected to skin-interfacing electrodes. Although ionotophoresis provides a method for controlled drug delivery, irreversible skin damage can occur from galvanic and pH burns resulting from electrochemical reactions that occur at the electrode and skin interface. This reaction precludes the use of this method when extended application times are needed to achieve prolonged systemic effects.

Sonophoresis is another active transport method that uses ultrasound varying in frequency from 20 kHz to 16 MHz to transport substances across the stratum corneum. Sonophoresis affects biological tissues by three main routes—thermal, cavitational and acoustic streaming. For example, ultrasound will increase the temperature of a given medium, and the absorption coefficient of that medium increases proportionally with ultrasound frequency. Cavitation can occur when ultrasound-induced pressure variation causes rapid growth and collapse of gas bubbles, causing structural alteration of the skin. Acoustic streaming, a phenomenon that affects surrounding tissue structure, can occur when shear stresses result from ultrasound reflections, distortions, and oscillations of cavitation bubbles. It has also been postulated that ultrasound interacts with the ordered lipids comprising the stratum corneum, forming an opening for drug passage. The interruption of the connective layer by any of the above-identified routes can lead to an area of skin that is predisposed to sloughing as well as bacterial and viral infiltration.

Microporation is an active transport method used to produce micropores in the stratum corneum. Microporation is accomplished by various means, including ablating the stratum corneum by local rapid heating of water, puncturing the stratum corneum with a micro-lancet calibrated to form a specific pore diameter, ablating the stratum corneum by focusing a tightly focused beam of sonic energy, hydraulically puncturing the stratum corneum with a high pressure fluid jet, and puncturing the stratum corneum with short pulses of electricity. Laser energy can also be used to cause microporation. Although the diameter of the hole can be controlled, microporation can cause irritation, damage and/or removal of stratum corneum cells.

Because of the inherent problems of the above-identified methods, a need exists for a safe and efficient transdermal drug delivery that eliminates side-effects and damage to the barrier function or appearance of the skin caused by drug administration. It would therefore be desirable to provide compositions, methods, and apparatuses to address these problems.

SUMMARY OF THE INVENTION

The problems associated with active intradermal or transdermal delivery of biologically active substances can be overcome by this invention, which relates to novel compositions, methods, and devices for photokinetic intradermal, transdermal, or transmembrane delivery of biologically active substances into or through the stratum corneum or a biological membrane without causing damage to this layer or underlying tissues, and without denaturation and/or degradation of the biologically active substance being administered.

The compositions, methods, and devices described herein preferably use pulsed incoherent light to focus and deliver biologically active substances through the outer most surface of the skin, and either locally into the epidermis layer of the skin (e.g., in cosmetic uses), or to an underlying tissue or blood vessel (e.g., in pharmaceutical uses), or from an extracellular environment to an intracellular environment. The depth of the delivery can be fine tuned or controlled to achieve the intended purpose. The intradermal drug deposition amount and transdermal flux rate can be predicted and controlled by modulation of the light energy. In some embodiments, compositions containing only biologically active substances are used as delivery media, whereas in other embodiments, biologically active substances used in combination with other components are used as delivery media.

Methods and devices employing pulsed incoherent light are used to actively transport a biologically active medium through the outer surface of the skin or cell membrane. This provides many advantages, including the ability to create a pathway for drug delivery without causing damage to the skin or membrane while being able to excite biologically active molecules without degrading or denaturing them. In addition, the rate of delivery of the biologically active component can be controlled, sustained, or substantially stopped, by modulating the wavelength, pulse rate, duty cycle and intensity of the light being used to photokinetically propagate the component into or through the skin or membrane. Finally, the use of a light pad containing more than one light source permits light to expose a biologically active medium over a well-defined surface area. The skin permeability can be enhanced through the use of compositions, methods and devices described herein.

Described herein is a novel platform technology pertaining to enhanced permeation kinetics of a compound into and through a tissue by the application of selected pulsed incoherent light (photokinetic method). The invention described herein has shifted the established tissue permeation paradigms away from the known limitations of established fundamental axioms, such as molecular weight limited permeation. This new photokinetic facilitated permeation technology allows for administration of a wide range of compounds having a wide range of molecular weights into and through intact tissues, without damage to the tissues or chemical changes to the molecule being delivered.

Therefore, one salient feature of the methods and systems of the invention is its superior safety feature, which can be particularly valuable for cosmetic applications. For example, since the penetration distance is a function of the time exposed to the light source (e.g., LED), the ability to regulate the flux rate of the biologically active substance, including the ability to target the delivery of the substance at a specific depth within the skin or epidermis, enables targeted delivery of certain cosmetically active substances to skin (without causing damages to the skin or leading to unpredictable effects resulting from systemic delivery of the substance).

Another safety feature of the subject delivery method resides in the fact that the delivery method does not damage human skin, and the active ingredients being delivered are not transformed to potentially harmful substances by the light energy.

Furthermore, using the subject dermal patch confers an additional layer of safety, since the subject dermal patch is produced from safe ingredients, many of which are natural, and contains no preservatives or other potentially harmful substances to the skin. The combination of the subject intradermal delivery technology with the subject dermal patch not only unexpectedly enhances delivery of the active ingredient, but also provides the above safety features valued in cosmetic industry.

Human skin possesses remarkably different drug permeation characteristics compared to animal skin. Animal skin permeation testing has little relevance in predicting human skin drug permeation. Partly because of the superior safety features of the invention and the irrelevance of animal skin permeation testing, no animal testing is needed for cosmetic products to be delivered to human through the subject methods and patches.

Thus, in one respect, the invention provides a method for photokinetic intradermal and/or transdermal delivery of a biologically active substance having a molecular weight of no less than 5800 Da to a subject, the method comprising: (1) preparing a formulation comprising the biologically active substance; (2) applying said formulation to a cellular surface on the skin of the subject; (3) illuminating said formulation on said cellular surface with a pulsed incoherent light having a selected wavelength, pulse rate and duty cycle; and, (4) allowing said biologically active substance in said formulation to permeate said cellular surface, thereby effecting photokinetic intradermal and/or transdermal delivery of the biologically active substance.

In certain embodiments, the biologically active substance has a molecular weight of no less than 10 kDa, 25 kDa, 50 kDa, 100 kDa, 150 kDa, 200 kDa, 250 kDa, 300 kDa, 350 kDa, 400 kDa, 500 kDa, 600 kDa, 700 kDa, 800 kDa, 900 kDa, 1,000 kDa, 1,500 kDa, 1,600 kDa, 2,000 kDa, 2,200 kDa, 2,500 kDa, or 3,000 kDa.

In certain embodiments, the subject is a human.

In certain embodiments, such as in pharmaceutical application, the subject is not a rodent (e.g., one or more of mouse, rat, squirrel, porcupine, beaver, chipmunk, guinea pig, vole, etc.).

In certain embodiments, the skin is non-porated intact skin, or the skin is porated by chemical, electrical, and/or physical means.

In certain embodiments, the formulation comprises a solution and a solvent.

In certain embodiments, the solvent is an aqueous or an organic solvent.

In certain embodiments, the aqueous solvent is an aqueous solution of ethyl lactate and proplyene glycol, water, or an aqueous solution of ethyl lactate or propylene glycol.

In certain embodiments, the formulation comprises a gelling agent.

In certain embodiments, the gelling agent comprises a hydroxyethyl cellulose, a cellulose derivative, a pectine, an agar, an alginic acid or a salt thereof, a guar gum, a polyvinyl alcohol, a polyethylene oxide, a propylene carbonate, a polyethylene glycol, a hexylene glycol sodium carboxymethylcellulose, a polyacrylate, a polyoxyethylene-polyoxypropylene, a block copolymer, a pluronics, a wood wax alcohol, a tyloxapol, and/or a hyaluronic acid (e.g., one with an average molecular weight of about 500 kDa, 600 kDa, 700 kDa, 800 kDa, 900 kDa, 1000 kDa, 1200 kDa, 1400 kDa, or 1,600-2,200 kDa).

In certain embodiments, the formulation further comprises a photocatalytic agent.

In certain embodiments, the photocatalytic agent has a band gap energy of between about 2.9 eV and about 3.2 eV, is a rutile form of titanium dioxide, or is an anatase form of titanium dioxide. For cosmetic applications, UV filters do not penetrate the skin.

In certain embodiments, the biologically active substance comprises a chemical, an antibiotic, a hormone, a peptide, an antibody, a protein, a plant extract (such as those used in the cosmetic industry), or a mixture thereof.

In certain embodiments, the biologically active substance comprises a drug.

In certain embodiments, the drug is a cytotoxic drug.

In certain embodiments, the drug comprises or further comprises an analgesic, an anaesthetic, an antacid, an anti-anxiety drug, an antiarrhythmics, an antibacterial, an antibiotic, an anticoagulant and thrombolytic, an anticonvulsants, an antidiarrheals, an antiviral, a barbiturate, and/or a vitamin.

In certain embodiments, the biologically active substance comprises or further comprises chemicals and said chemicals comprise a polar or a non-polar compound.

In certain embodiments, the polar compound is selected from the group consisting of theophylline-7 acetic acid, sodium ascorbyl phosphate, ascorbic acid, ascorbyl palmitate, pyridoxine, nicotinic acid, and lidocaine.

In certain embodiments, the non-polar compound is selected from the group consisting of theobromine, theophylline, caffeine, and nicotinamide.

In certain embodiments, the biologically active substance comprises sodium hyaluronate (such as one with a M.W. of no less than 20 kDa, 50 kDa, 100 kDa, 200 kDa, 400 kDa, 500 kDa, 1000 kDa, 1250 kDa, 1500 kDa, 1600 kDa, 2000 kDa, 2100 kDa, 2200 kDa, 2500 kDa, 3000 kDa, 3500 kDa, 4000 kDa, 4500 kDa, 5000 kDa or more).

In certain embodiments, the biologically active substance is a cosmetic agent, or a therapeutic agent.

In certain embodiments, the biologically active substance comprises or
further comprises: (1) a peptide selected from the group consisting of Gly-Tyr, Val-Tyr-Val, Tyr-Gly-Gly-Phe-Met (SEQ ID NO: 1), Tyr-Gly-Gly-Phe-Leu (SEQ ID NO: 2), and Asp-Arg-Val-Tyr-Ile-His-Pro-Phe (SEQ ID NO: 3); (2) a hormone selected from the group consisting of methionine enkephalin acetate, leucine enkephalin, angiotensin II acetate, β-estradiol, methyl testosterone, and progesterone; or, (3) a protein selected from the group consisting of enzymes, non-enzymes, antibodies, and glycoproteins.

In certain embodiments, the cellular surface is a cell membrane.

In certain embodiments, the pulsed incoherent light is selected from the group consisting of fluorescent, ultraviolet, visible, near infrared, LED (light emitting diode), and halogen light.

In certain embodiments, the fluorescent light has a wavelength range from about 260 nm to about 760 nm.

In certain embodiments, the ultraviolet light has a wavelength range from about 340 nm to about 900 mm.

In certain embodiments, the visible light has a wavelength range from about 340 nm to about 900 nm.

In certain embodiments, the near infrared light has a wavelength range from about 340 nm to about 900 nm.

In certain embodiments, the halogen light has a wavelength range from about 340 nm to about 900 nm.

In certain embodiments, the wavelength is selected from the group consisting of 350 nm, 390 nm, 405 nm, and 450 nm.

In certain embodiments, the pulse rate is between about 1.7 cycles per second (cps) and about 120 cps, or about 1.7 cps and about 80 cps.

In certain embodiments, the pulse rate is between about 24-100 cps.

In certain embodiments, the duty cycle is between about 50% and about 75%.

In other embodiments, a discrete On time and a discreet OFF time, in the range of, for example, 1% ON/99% OFF to 99% ON/1% OFF (including any integer values in between, such as 2%ON98%OFF, 5%ON95%OFF, 10%ON90%OFF, 15%ON85%OFF, etc.) are all contemplated embodiments of the invention.

In certain embodiments, the method further comprises adjusting the transdermal flux rate of the biologically active substance by modulating the light energy.

In certain embodiments, the method further comprises adjusting the flux rate of the biologically active substance by modulating the light energy, in order to deliver all or substantially all biologically active substance intradermally (within the skin).

In certain embodiments, the formulation comprises a dermal patch, said dermal patch containing a red algae polysaccharide-based matrix, wherein said red algae polysaccharide is an extract of *Chondrus crispus* at 2% by weight of the dermal patch.

In certain embodiments, the concentration (by weight) of *Chondrus crispus* is about 0.5%, 1.0%, 1.5%, 2.0%, 2.5%, 3.0%, 3.5%, or about 4%. Any two values may also serve at the lower and higher ends of a suitable range. In certain embodiments, the concentration (by weight) of *Chondrus crispus* is about 1.5%-2.5%, preferably 2.0%.

In certain embodiments, such as in cosmetic application, the dermal patch is disposable (e.g., after single use or limited time of uses), biodegradable, environmentally safe, and/or produced using essentially natural ingredients. Preferably, the biologically active substance (e.g., the cosmetic active ingredient) is present in the dermal patch at a higher amount (e.g., 20-fold excess, 10-fold excess, 5-fold excess, etc.) compared to the amount to be delivered, so as to maintain relatively constant rate of release of the active ingredient.

In certain embodiments, the dermal patch further comprises methylpropanediol and glycerine as moisturising and anti-microbial ingredients.

In certain embodiments, the dermal patch further comprises butylene glycol and sorbitol as moisturising ingredients.

In certain embodiments, the dermal patch comprises water, methylpropanediol, glycerin, *Chondrus crispus*, and optionally a preservative.

In certain embodiments, the dermal patch comprises (as weight %) 67% water, 10% methylpropanediol, 20% glycerin, 2% *Chondrus crispus* and optionally a preservative.

In certain embodiments, the dermal patch comprises water, butylene glycol, sorbitol, *Chondrus crispus* and optionally a preservative.

In certain embodiments, the dermal patch comprises (as weight %) 67% water, 10% butylene glycol, 20% sorbitol, 2% *Chondrus crispus* and optionally a preservative.

In certain embodiments, the dermal patch comprises no preservative.

In certain embodiments, the dermal patch is prepared according to a processing comprising the following steps: (1) providing a water mixture of the vegetable matrix, excipients and active ingredients; (2) heating the mixture to a temperature between 30-90° C.; (3) casting the mixture in a mould while keeping the temperature between 30 and 90° C.; and, (4) cooling the mixture to about room temperature.

In certain embodiments, the mixture is heated at 90° C. under mixing.

In certain embodiments, in step (3), the temperature is maintained at 50-60° C.

In certain embodiments, the mixing step (1) is performed in a planetary mixer equipped with a jacketing for heating under controlled temperature.

In certain embodiments, in step (3), the mixture is casted in a plastic mould for blisters.

In certain embodiments, the method further comprises the application of a sheet of aluminium/polythene tie layer to seal the blister and the die-cut of the blister to obtain the desired final shape of the finished product.

In a related aspect, the invention provides a method for photokinetic intradermal and/or transdermal delivery of a biologically active substance to a subject, the method comprising: (1) preparing a dermal patch comprising the biologically active substance, wherein the dermal patch comprises a red algae polysaccharide-based matrix, and wherein said red algae polysaccharide is an extract of *Chondrus crispus* at 2% by weight of the dermal patch; (2) applying said dermal patch to a cellular surface on the skin of the subject; (3) illuminating said dermal patch on said cellular surface with a pulsed incoherent light having a selected wavelength, pulse rate and duty cycle; and, (4) allowing said biologically active substance in said dermal patch to permeate said cellular surface, thereby effecting photokinetic intradermal and/or transdermal delivery of the biologically active substance.

Specific embodiments of this aspect of the invention are described above and not repeated verbatim here.

Another aspect of the invention provides a device for photokinetic intradermal and/or transdermal delivery of a biologically active substance having a molecular weight of no less than 5800 Da to a subject, said device comprising: (1) a generator that provides an oscillating electrical pulse; (2) at least one light emitting diode that receives the oscillating electrical pulse and responds by providing an incoherent light; and, (3) a donor cell that holds a formulation comprising the biologically active substance, wherein the donor cell is positioned to receive the incoherent light.

Specific embodiments of this aspect of the invention are described above and not repeated verbatim here.

Another aspect of the invention provides a device for photokinetic intradermal and/or transdermal delivery of a biologically active substance to a subject, said device comprising: (1) a generator that provides an oscillating electrical pulse; (2) at least one light emitting diode that receives the oscillating electrical pulse and responds by providing an incoherent light; and, (3) a donor cell that holds a dermal patch comprising the biologically active substance, wherein the dermal patch comprises a red algae polysaccharide-based matrix, wherein said red algae polysaccharide is an extract of *Chondrus crispus* at 2% by weight of the dermal patch, and wherein the donor cell is positioned to receive the incoherent light.

In certain embodiments, the generator is a repeat cycle square wave pulse generator.

In certain embodiments, the device further comprises a light pad, wherein at least one light emitting diode is embedded in said light pad.

In certain embodiments, the light pad is comprised of an optically clear material.

In certain embodiments, the optically clear material is poly(methylmethacrylate) or silicone rubber.

Other specific embodiments of this aspect of the invention are described above and not repeated verbatim here.

It should be understood that any embodiments of the invention described herein, including those described under different aspects of the invention, can be combined with one or more other embodiments of the invention.

BRIEF DESCRIPTION OF THE DRAWINGS

FIG. 10A shows transdermal permeation of botulinum toxin type A at 24 hours of photokinetic conditions of light wavelengths 405 nm and 450 nm pulsed at 24 cps and 100 cps compared to passive control. The four photokinetic conditions all produced significant increases in transdermal flux compared to passive permeation ($p<0.001$).

FIG. 10B shows intradermal deposition of botulinum toxin type A at 24 hours of photokinetic conditions of light wavelengths 405 nm and 450 nm pulsed at 24 cps and 100 cps compared to passive control. The photokinetic conditions of 450 nm light pulsed at 24 and 100 cps both produced significant increases in achievable tissue deposition of botulinum toxin type A compared to passive tissue deposition ($p<0.05$).

DETAILED DESCRIPTION OF THE INVENTION

1. Overview

Figure 1:
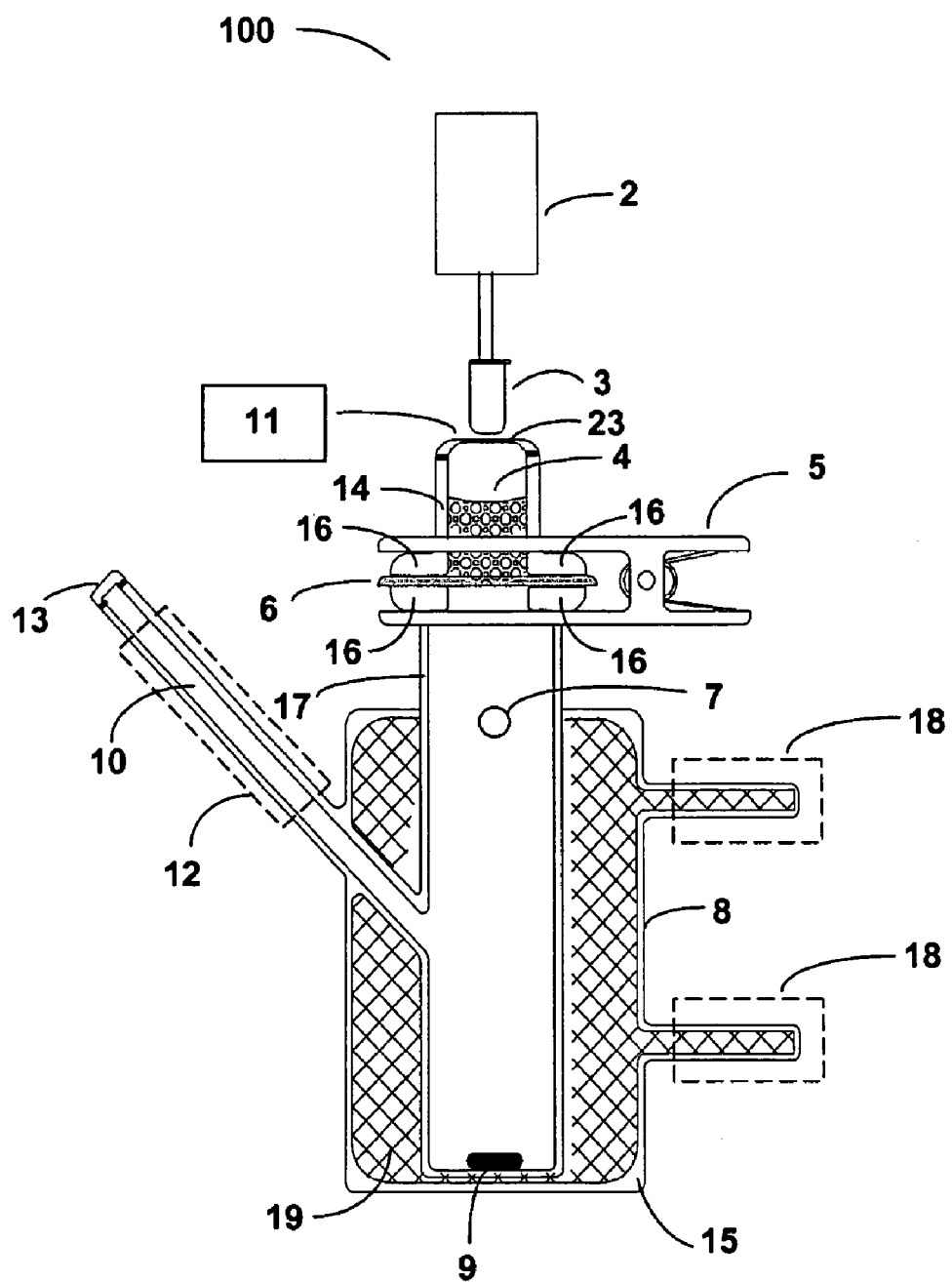
FIG. 1 shows a Franz skin diffusion device equipped with a light source to generate pulses of defined wavelengths for testing of biologically active substances.

Optimum therapeutic outcomes require not only proper drug selection but also effective drug delivery.

Oral delivery (e.g. pills) has been considered as the most appropriate method of drug administration for decades. Most of the drugs that cannot be taken by oral delivery have traditionally been administered by injections with hypodermic needles. However, hypodermic injections have many disadvantages, such as pain, potential infections and the requirement for medical expertise to complete the injection process (Park et al. 2005).

The human skin is also a readily accessible surface for drug delivery. Over the past three decades, developing controlled drug delivery has become increasingly important in the pharmaceutical industry. The pharmacological response, both the desired therapeutic effect and the undesired adverse effect, of a drug is dependent on the concentration of the drug at the site of action, which in turn depends upon the dosage form and the extent of absorption of the drug at the site of action.

Skin of an average adult body covers a surface of approximately 2 m$^2$, and receives about one-third of the blood circulating through the body. Skin contains an uppermost layer, epidermis which has morphologically distinct regions; basal layer, spiny layer, stratum granulosum and upper most stratum corneum, it consists of highly cornified (dead) cells embedded in a continuous matrix of lipid membranous sheets. These extracellular membranes are unique in their compositions and are composed of ceramides, cholesterol and free fatty acids. The human skin surface is known to contain, on an average, 10-70 hair follicles and 200-250 sweat ducts on every square centimeter of the skin area. It is one of the most readily accessible organs of the human body. The potential of using the intact skin as the port of drug administration to the human body has been recognized for several decades, but skin is a very difficult barrier to the ingress of materials allowing only small quantities of a drug to penetrate over a period of time.

Facilitated or "active" transdermal methods wherein electrical (iontophoresis) or sound energy (phonophoresis or sonophoresis) is added into the system have been employed as methods to increase the drug flux across the skin. In the absence of skin poration side effects with these methods (electroporation caused by excessive electrical energy or destructive micro-bubble formation within the epidermis from cavitation induced by sound energy) the drug flux across intact skin remains limited by the drug molecular weight. It is widely accepted and understood by those familiar with the art that there is a practical upper molecular weight limit for drugs permeating though intact human skin. This upper molecular weight limit is considered to be about 500 Daltons (Da) with considerable diminished permeation in drugs with larger molecular weights. This molecular weight limiting property is commonly referred to in the art as the "500 Dalton Rule" wherein as the molecular weight of the drug increases the expected permeation through human skin decreases and generally falls to insignificant amounts as the molecular weight approaches 500 Da.

Transdermal drug delivery (TDD)—the delivery of drugs across the skin and into systemic circulation—is distinct from topical drug penetration or intradermal delivery, which targets local areas, such as delivery or application of cosmetic ingredients to the skin. Transdermal drug delivery takes advantage of the relative accessibility of the skin, and is an alternative route of drug administration to pills and injections. This method operates by delivering drugs into the human body across the skin using devices such as a patch (e.g., a transdermal patch). The transdermal patches have the ability to eliminate at least some of the problems mentioned above. They usually contain a drug reservoir that can maintain a steady drug flow of up to about one week (Prausnitz et al., 2004). Although these patches have proven to be very successful, they depend on the characteristics of the drug, e.g., the size, charge, and even some physiochemical properties (Naik et al., 2000) to be successful. This is largely due to the barrier function of the skin represented by the outer layer of the skin, the stratum corneum, which generally allows diffusion of only small molecular weight solutes (less than 500 Da), with the ability to allow penetration of certain oil-soluble solutes (Shah 2003). To circumvent this diffusion limitation, methods have been developed to more effectively deliver drugs across the stratum corneum, including chemical enhancers (Williams & Barry 2004) or physical enhancer techniques, e.g., iontophoresis (Kalia et al. 2004) and ultrasound (Prausnitz et al. 2004). However, the high cost, complexity, and the difficulty in dealing with these methods at home pose problems for potential users.

Transdermal drug delivery offers several important advantages over more traditional dosage forms. The steady permeation of drug across the skin allows for more consistent serum drug levels, often a goal of therapy. Intravenous infusion also achieves consistent plasma levels, but it is more invasive than transdermal drug delivery.

The lack of peaks in plasma concentration can reduce the risk of side effects. Thus, drugs that require relatively consistent plasma levels are very good candidates for transdermal drug delivery. In addition, if toxicity were to develop from a drug administered transdermally, the effects could be limited by removing the patch.

Another advantage is convenience, especially notable in patches that require only once weekly application. Such a simple dosing regimen can aid in patient adherence to drug therapy. Transdermal drug delivery can be used as an alternative route of administration to accommodate patients who cannot tolerate oral dosage forms. It is of great advantage in patients who are nauseated or unconscious. Drugs that cause gastrointestinal upset can be good candidates for transdermal delivery because this method avoids direct effects on the stomach and intestine. Drugs that are degraded by the enzymes and acids in the gastrointestinal system may also be good targets. First pass metabolism, an additional limitation to oral drug delivery, can be avoided with transdermal administration. Thus, in certain embodiments, the drugs/molecules to be delivered using the instant methods and systems are such drugs, or are intended to be delivered to such patient populations.

Other advantage includes suitability for using with drug candidates with short half-life and low therapeutic index.

The first TDD System (TDDS) was developed for scopolamine for motion sickness in 1981. Since then, many TDDS have appeared in market with great success. In spite of the therapeutic success achieved in last 28 years by using TDDS, the number of TDDS available in the market place is comparatively very few. This is mainly due to inherent limitations of the TDDS listed below.

One of the greatest disadvantages to transdermal drug delivery is the possibility that a local irritation may develop at the site of application. Erythema, itching, and local edema can be caused by the drug, the adhesive, or other excipients in the patch formulation. For most patients, site rotation can minimize irritation. However, some patients develop severe allergic reactions to transdermal patches, and, in these cases, therapy must be discontinued.

Another significant disadvantage of transdermal drug delivery is that the skin's low permeability limits the number of drugs that can be delivered in this manner. Because the skin serves protective functions, it inhibits compounds from crossing it. Many drugs with a hydrophilic structure permeate the skin too slowly to be of therapeutic benefit. Drugs with a lipophillic character, however, are better suited for transdermal delivery.

In order to maintain consistent release rates, transdermal patches may contain a surplus of active molecule. A stable concentration gradient is the mechanism used to maintain consistent release rates and constant serum drug levels. Most transdermal patches contain 20 times the amount of drug that will be absorbed during the time of application. Thus, after removal, most patches contain at least 95% of the total amount of drug initially in the patch. Therefore; patients must exercise care when disposing of patches. For example, each patch should be folded in half and the adhesive sides should be stuck together. As an additional precaution, patches may be flushed down the toilet rather than discarded in household trash, where children and pets may find them and ingest the remaining drug.

Damage to a transdermal patch, particularly a membrane or reservoir patch, can result in poor control over the release rate. The release rate from a damaged patch would more likely be controlled by the skin than the patch, resulting in a higher, perhaps toxic, rate of drug delivery. Patients should be advised to discard a patch if the outer packaging or the patch itself appears damaged or altered in any way.

Other limitations for TDDS include factors that limit a drug candidate's ability to be incorporated into a transdermal delivery system, such as: higher molecular weight (e.g., >500 Da) that renders the drug molecule harder to penetrate the stratum corneum; very low or high partition coefficient for certain drugs, which prevents such drugs to reach systemic circulation; and high melting drugs due to their low solubility both in water and fat. Such candidate drugs with one or more of these properties may not be efficiently delivered across the skin without effectively making suitable modifications in the conventional transdermal delivery systems.

There are two concepts in the design of transdermal delivery, namely, the reservoir type and the matrix type. Others are actually extensions of these two concepts and both involve diffusion of drug molecule from the topically applied donor reservoir and into and through the skin barrier.

Modulation of formulation excipients and addition of chemical enhancers, such as fatty acids, surfactants, esters and alcohols that exert their action via a temporary alteration of barrier properties of the stratum corneum by various mechanisms, including enhancing solubility, partitioning the stratum corneum, fluidizing the crystalline structure of the stratum corneum and causing dissolution of stratum corneum lipids can enhance drug flux. However, due to low permeability coefficients of macromolecules, the enhancement effects required to ensure delivery of pharmacologically effective concentrations are likely to be beyond the capability of chemical enhancers tolerated by the skin. Therefore, several new active transport technologies have been developed for the transdermal delivery of "troublesome" drugs as the development of modified novel physical techniques have overcome the limitations of chemical enhancement techniques.

In transdermal technology, emphasis is placed on producing therapeutic drug flux rates using a limited skin surface area with minimal skin irritating or damaging side effects. Applicants have previously described a method of enhanced or facilitated transdermal drug delivery called "photokinetic" drug delivery (see US2004-0131687A1, U.S. Pat. Nos. 7,458,982 and 7,854,753, and EP 1556061 B1, including all examples and drawings thereof, are all incorporated herein by reference) for delivery of biologically active substances using pulsed incoherent light, wherein the application of pulsed incoherent light onto a drug on the surface of intact skin allows or facilitates the permeation of that drug into and through the skin.

More than 80% of all traded drugs have molecular weights below 450 Da. There are therapeutic agents with larger molecular weights, but these agents are generally considered well beyond the accepted known limits of molecular-weight-limited skin permeation. Against this background, and to the complete surprise and utter amazement of the Applicants, it was found that the photokinetic system can be utilized for skin permeation (e.g., intradermal and transdermal delivery) of large to very large molecular weight drugs, such as drugs in the molecular weight range of 7,676 Da for insulin like growth factor-1 (IGF-1) up to and including 2,180,000 Da (2180 kDa) hyaluronic acid (HA), into and through intact skin. This result is surprising and completely unexpected, partly because the increase in molecular weight limits for intra- and transdermal drug delivery are several thousand times more than the widely accepted 500 Da upper molecular weight limit.

Thus one aspect of the invention provides method for photokinetic intradermal and/or transdermal delivery of a biologically active substance having a molecular weight of no less than 5800 Da to a subject, the method comprising: (1) preparing a formulation comprising the biologically active substance; (2) applying said formulation to a cellular surface on the skin of the subject; (3) illuminating said formulation on said cellular surface with a pulsed incoherent light having a selected wavelength, pulse rate and duty cycle; and, (4) allowing said biologically active substance in said formulation to permeate said cellular surface, thereby effecting photokinetic intradermal and/or transdermal delivery of the biologically active substance.

In certain embodiments, the biologically active substance has a molecular weight of no less than 10 kDa, 25 kDa, 50 kDa, 100 kDa, 150 kDa, 200 kDa, 250 kDa, 300 kDa, 350 kDa, 400 kDa, 500 kDa, 600 kDa, 700 kDa, 800 kDa, 900 kDa, 1,000 kDa, 1,500 kDa, 1,600 kDa, 2,000 kDa, 2,200 kDa, 2,500 kDa, or 3,000 kDa.

Another aspect of the invention is partly based on the unexpected results arising from combining the photokinetic drug delivery method/system with a dermal patch described in WO 09/124,763 A2.

Typically, when drugs are applied to the skin, they may be formulated in a liquid or gel form or in some physical containment method such as the common transdermal patch. Also, typically the topical application method may have an effect on the permeation of the drug from the topical application and into the skin. Micro-emulsion drug compositions generally provide better transdermal flux than water based gels or drug/patch combinations.

Applicants have examined the combination effects of a particular drug patch (described in WO 09/124,763 A2) containing 2,180 kDa hyaluronic acid with photokinetic technology, and have found that this combination has surprisingly better permeation results (e.g., up to an increase of about 200-300%) when compared with the same drug in a gel or emulsion formulation.

Thus another aspect of the invention provides method for photokinetic intradermal and/or transdermal delivery of a biologically active substance to a subject, the method comprising: (1) preparing a dermal patch comprising the biologically active substance, wherein the dermal patch comprises a red algae polysaccharide-based matrix, and wherein said red algae polysaccharide is an extract of *Chondrus crispus* at 2% by weight of the dermal patch; (2) applying said dermal patch to a cellular surface on the skin of the subject; (3) illuminating said dermal patch on said cellular surface with a pulsed incoherent light having a selected wavelength, pulse rate and duty cycle; and, (4) allowing said biologically active substance in said dermal patch to permeate said cellular surface, thereby effecting photokinetic intradermal and/or transdermal delivery of the biologically active substance.

In a related aspect, the invention also provides a device for photokinetic intradermal and/or transdermal delivery of a biologically active substance having a molecular weight of no less than 5800 Da to a subject, said device comprising: (1) a generator that provides an oscillating electrical pulse; (2) at least one light emitting diode that receives the oscillating electrical pulse and responds by providing an incoherent light; and, (3) a donor cell that holds a formulation comprising the biologically active substance, wherein the donor cell is positioned to receive the incoherent light.

In yet another related aspect, the invention provides a device for photokinetic intradermal and/or transdermal delivery of a biologically active substance to a subject, said device comprising: (1) a generator that provides an oscillating electrical pulse; (2) at least one light emitting diode that receives the oscillating electrical pulse and responds by providing an incoherent light; and, (3) a donor cell that holds a dermal patch comprising the biologically active substance, wherein the dermal patch comprises a red algae polysaccharide-based matrix, wherein said red algae polysaccharide is an extract of *Chondrus crispus* at 2% by weight of the dermal patch, and wherein the donor cell is positioned to receive the incoherent light.

More detailed aspects and embodiments of the inventions are set forth herein, including in the examples.

2. Definitions

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular. Generally, nomenclatures used in connection with, and techniques of, column chromatography, optics, chemistry, peptide and protein chemistries, nucleic acid chemistry and molecular biology described herein are those well known and commonly used in the art.

The following terms, unless otherwise indicated, shall be understood to have the following meanings:

The term "biologically active substance" refers generally to any chemical, drug, antibiotic, peptide, hormone, protein, DNA, RNA and mixtures thereof that affects biological pathways or interacts with cellular components. In certain embodiments, the biologically active substance comprises one or more cosmetic active ingredients.

The term "chemical" denotes any naturally found or synthetically made or extracted small molecule or polymer (including naturally extracted cosmetic ingredients or cosmetic ingredients extracted from a natural source, such as polyphenols, plant extracts, etc.). In certain embodiments, a chemical may also include certain biofermentation compounds (such as sodium hyaluronate, etc.).

A chemical can be a polar (hydrophilic), non-polar (hydrophobic), oleophobic or oleophilic compound. Although not an exhaustive list, examples of polar compounds include polyphenols, phytosterols, theophylline-7-acetic acid, sodium ascorbyl phosphate, ascorbic acid, ascorbyl palmitate, pyridoxine, nicotinic acid and lidocaine. Examples of non-polar compounds include theobromine, theophylline, caffeine and nicotinamide. Oleophobic compounds are those compounds lacking affinity for oils and oleophilic compounds are any compounds that have a stronger affinity for oils over that of water. Accordingly, the invention described herein is particularly useful for transport of compounds with chromophores, which can be polar, non-polar, oleophobic, including fluorochemicals, and oleophilic.

The term "drug" denotes any natural or synthetic compound used for therapeutic treatment in mammals. Examples of drugs include, but are not limited to, analgesics, antacids, antianxiety drugs, antiarrhythmics, antibacterials, antibiotics, anticoagulants and thrombolytics, anticonvulsants, antidepressants, antidiarrheals, antiemetics, antifungals, antihistamines, antihypertensives, anti-inflammatories, antieoplastics, antipsychotics, antipyretics, antivirals, barbiturates, beta-blockers, bronchodilators, cold cures, corticosteroids, cough suppressants, cytotoxics, decongestants, diuretics, expectorant, hormones, hypoglycemic s, immunosuppressives, laxatives, muscle relaxants, sedatives, sex hormones, sleeping drugs, tranquilizer and vitamins.

Vitamins are organic chemicals that are essential for nutrition in mammals and are typically classified as fat-soluble or water-soluble. Vitamins required to maintain health in humans include, but are not limited to, vitamin A (retinol), precursor to vitamin A (carotene), vitamin $B_1$ (thiamin), vitamin $B_2$ (riboflavin), vitamin $B_3$ (nicotinic acid), vitamin B (pantothenic acid), vitamin C (ascorbic acid), vitamin D (calciferol), vitamin E (tocopherol), vitamin H (biotin) and vitamin K (naphthoquinone derivatives).

The term "antibiotic" refers to any natural or synthetic substance that inhibits the growth of or destroys microorganisms in the treatment of infectious diseases. Although not an exhaustive list, examples of antibiotics include amoxycillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, teracycline, coxycycline, chloramphenicol and zithromycin.

The term "peptide" refers to a compound that contains 2 to 50 amino acids and/or imino acids connected to one another. The amino acids can be selected from the 20 naturally occurring amino acids. The twenty conventional amino acids and their abbreviations follow conventional usage. See Immunology—A Synthesis ($2^{nd}$ Edition, E. S. Golub and D. R. Gren, Eds., Sinauer Associates, Sunderland, Mass. (1991)), which is incorporated herein by reference. The amino acids can also be selected from non-natural amino acids such as those found at the Sigma-Aldrich web site, including without limitation: β-amino acids ($b^3$ and $b^2$), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids, diamino acids (see Sigma-Aldrich ChemFiles Vol. 1 No. 5 (Unnatural Amino Acids); Vol. 2 No. 4 (Unnatural Amino Acids II); and Vol. 4 No. 5 (Unnatural Amino Acids: Tools for Drug Discovery). Although not an exhaustive list, examples of peptides include glycine-tyrosine, valine-tyrosine-valine, tyrosine-glycine-glycine-phenylalanine-methionine, tyrosine-glycine-glycine-phenylalanine-leucine and aspartic acid-arginine-valine-tyrosine-isoleucine-histidine-proline-phenylalanine.

"Preservative(s)" as used herein include the ones listed in the following web site http://ec.europa.eu/consumers/cosmetics/cosing/index.cfm?fuseaction=search.results&annex_v1=VI&search. A PDF copy of which is attached as appendix. Also see European Cosmetics Directive 76/768/EEC—Annex VI part 1 ("list of preservatives allowed" from "List of preservatives which cosmetic products may contain").

Representative preservatives include: parabens (methyl-, ethyl-, propyl-, butylparaben); urea-derivatives (imidazolidinyl urea, diazolidinyl urea); isothiazolones (methyl-chloro-, methyl-isothiazolinone); halogen-organic actives (iodopropynyl butylcarbamate, methyldibromo glutaronitrile); organic acids & others (sodium benzoate, chloracetamide, EDTA, phenoxyethanol, triclosan, DMDM-hydantoin, quaternium-15).

In certain embodiments, preservatives may also comprise certain natural components that reinforce the anti-microbial efficacy, such as extracts (grapefruit seed, rosemary); essential oils (tea tree, neem seed, thyme); vitamins (vitamin E, vitamin C), alcohols, glycols, or glycerin, etc. In other embodiments, preservatives do not include such natural components.

The term "hormone" refers to a substance that originates in an organ, gland, or part, which is conveyed through the blood to another part of the body, stimulating it by chemical action to increase functional activity or to increase secretion of another hormone. Although not an exhaustive list, examples of hormones include methionine enkephalin acetate, leucine enkephalin, angiotensin II acetate, β-estradiol, methyl testosterone, progesterone and insulin.

A polypeptide is defined as a chain of greater than 50 amino acids and/or imino acids connected to one another.

A protein is a large macromolecule composed of one or more polypeptide chains. The term "isolated protein" is a protein that by virtue of its origin or source of derivation (1) is not associated with naturally associated components that accompany it in its native state, (2) is free of other proteins from the same species, (3) is expressed by a cell from a different species, or (4) does not occur in nature. Thus, a protein that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The terms DNA and RNA as referred to herein mean deoxyribonucleic acid and ribonucleic acid, respectively. The term "polynucleotide" means a polymeric form of nucleotides of at least 10 bases in length, either ribonucleotides or deoxynucleotides or a modified form of either type of nucleotide. The term includes single and double stranded forms.

The term "molecular weight" refers to the sum of the atomic weights of all atoms constituting a molecule, and can be numerically expressed in Dalton (Da). For example, certain low molecular weight biologically active compounds may include compounds having a molecular weight of less than 1,000 Da (1 kDa). By contrast, certain large molecular weight biologically active compounds may include drugs having a molecular weight greater than 1,000 Da. In the one embodiment of the invention, large molecular weight biologically active compounds include compounds having a molecular weight greater than that of insulin (which has a molecular weight of about 5,730 Da). In certain embodiments, a large molecular weight biologically active compound includes insulin like growth factor-one (IGF-1) with a molecular weight of about 7,649 Da, human growth hormone (HGH) with a molecular weight of about 22,124 Da (22 kDa), Botulinum Toxin Type A with a molecular weight of about 69,000 Da (69 kDa), and various forms of hyaluronic acid (HA) with molecular weights between 150,000 Da (150 kDa) and 2,180,000 Da (2,180 kDa).

The term "intact skin" refers to skin that retains its natural barrier function, and has not been altered by chemical, physical poration or has not been degraded by prolonged storage or otherwise altered in a way that may harm the barrier function. Intact skin has not been subjected to barrier function damage caused by, but not limited to, freeze/thaw ice crystal damage, electroporation, laser poration or obliteration, physical poration by micro-needles, enzymatic or chemically induced degradation, or any other method that may irreversibly degrade normal barrier function of the skin.

The term "passive transdermal delivery" refers to drug delivery wherein a drug is placed on the surface of a skin and permeates into the skin as a function of concentration gradient between the higher drug concentration on the skin surface and the lower drug concentration within the skin. Typical transdermal patch systems that use passive transdermal drug delivery may include nicotine patches, estradiol patches and fentanyl patches that are applied to intact skin and result in the drug permeating into the skin.

The term "active transdermal delivery" refers to methods wherein energy in some forms is imposed on a transdermal system, resulting in an increase in drug flux into and through the skin.

Gelling agents according to this invention are compounds that can behave as reversible or non-reversible networks. Under certain conditions, a gelling agent can be placed in a solvent to form a viscous solution. Under other conditions, that same gelling agent can be placed in the same or different solvent to form a gel. The role of gelling agents according to the invention is to prevent evaporation loss of the biologically active substance in the appropriate solvent. Examples of gelling agents include, but are not limited to, hydroxyethyl cellulose, Natrasol®, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols, tyloxapol, and carbomers.

The term "photocatalytic agent" refers to any semiconductor having a wide band gap energy. In an embodiment of the invention, the band gap energy is on the order of about 2.9-3.2 eV. A band gap on this order allows infrared and the entire visible spectrum to be transmitted upon excitation of an electron from the valence band to the conduction band. Without being bound by theory, pulsed incoherent light energy that is stored and released from the wide band gap semiconductor can enhance the bond vibration of a biologically active molecule also present during this excitation. The stimulation of active molecules with the transfer of energy from the semiconductor at discrete wavelengths and pulse rates can enhance the transport of that molecule across biological membranes, while the semiconductor can also protect the skin from harmful ultraviolet (UV) rays by absorbing UV light. By modulating the wavelength of excitation with that of the band gap energy, the production of free radicals is avoided entirely. Accordingly, the use of rutile form of titanium dioxide ($TiO_2$) as the photocatalytic agent is preferred because it has a band gap energy of about 2.9 to 3.0 eV. Other photocatalytic agents suitable for this invention include, but are not limited to, anatase $TiO_2$, brookite $TiO_2$, ZnO, $ZrO_2$ and $Sc_2O_3$. According to the invention, doped semiconductors can also be used.

In some embodiments, the "photocatalytic agent" does not produce a photochemical reduction nor is it intended to produce a photochemical reaction, but serves as a light scattering agent within the composition, and acts as a light absorbing/energy releasing medium to enhance the photokinetic activity. In certain embodiments, the "photocatalytic agent" herein is absent or not used in the photokinetic delivery method.

It should be noted that the "photocatalytic agent" here does not cause a photochemical reaction, and thus the photokinetic delivery system herein is not a form of photodynamic therapy. The photokinetic system of the invention does not cause tissue damage or chemically alter the drug being transported. For example, the ELISA analytical methods used for certain drugs being delivered tend to show that the drug has not been chemically altered, as the ELISA method would not work on a chemically altered drug (since it would change the binding property of the drug in the ELISA assay). This is consistent with Applicants' observations of pharmaceutical experiments performed in diabetic rats, wherein the blood sugar levels were reduced with insulin delivered by the photokinetic method (Kulp et al., Photokinetic Transdermal Drug Delivery (PTDD)—A Novel Platform Technology for Insulin Delivery.: Diabetes Technology Society Meeting, Nov. 11-13, 2010). In addition, compounds analyzed by HPLC methods did not show divergent peaks in the chromographs of the analyte, further demonstrating intact unaltered/undamaged molecules after delivery by the instant photokinetic method.

Additional data shows that the subject system does not change the tissue morphology as determined by histological examination (Koutrouvelis et al., Photokinetic Transdermal Delivery of Cyanocobalamin.: Proceedings of The Controlled Release Society, 2008). This feature can be particularly beneficial in satisfying the safety requirements, when applying the subject method in, for example, the cosmetic field.

The term "solvent" according to the invention is any aqueous or organic solvent that can be combined with the biologically active agent to form a solution. In one embodiment, the aqueous solvent is water. In another embodiment, the solvent can be an aqueous solution of either ethyl lactate or propylene glycol, both of which act as permeation enhancers. In other embodiments, the solvent comprises squalene, squalane, and/or olive glycerides or similar compounds that can assist in dissolving the biologically active ingredient (such as an cosmetic components). These agents may also enhance passage of the biologically active ingredient through the skin layers. Alternately, the term "solvent" can also mean an adhesive used to embed a biologically active substance, for example, in a patch. Solvent can also refer to a pharmaceutically-acceptable medium combined with the biologically active substance to be used in powder form.

In another embodiment, the biologically active substance can be emulsified. For example, lipophilic compounds, such as vitamins A, D, and E or olive glycerides, can be dispersed in an aqueous solvent to which an emulsifying agent, such as surfactants or self emulsifying oils can be added.

Likewise, in the absence or presence of a solvent, the biologically active agent according to the invention can also be combined with a carrier or adjuvant, a substance that, when added to a therapeutic, speeds or improves its action (The On-Line Medical Dictionary website: www dot cancerweb dot ncl dot ac dot uk, under subfolder/omdlindex.html). Examples of adjuvants include, for example, Freud's adjuvant, ion exchanges, alumina, aluminum stearate, lecithin, buffer substances, such as phosphates, glycine, sorbic acid, potassium sorbate, partial glyceride mixtures of saturated vegetable fatty acids, glycerin, waters, salts or electrolytes, such as Protamine sulfate, disodium hydrogen phosphate, sodium chloride, zinc salts, colloidal silica, magnesium, trisilicate, celluslose-based substances and polyethylene glycol. Adjuvants for gel base forms may include, for example, sodium carboxymethylcelluslose, polyacrylates, polyoxyethylene-polyoxypropylene-block copolymers, polyethylene glycol and wood wax alcohols.

Although not required to facilitate transdermal delivery, skin-penetrating agents, for example, propylene glycol, DMSO, oleic acid, laurocapram (Azone), cineol, liposomes and nanosomes, can also be present in the compositions according to the invention.

The term "donor solution" or "delivery medium" comprises the biologically active substance itself or any mixture of this substance with a solvent, a gelling agent, a photocatalytic agent, a carrier or adjuvant, a skin-penetrating agent, a membrane-penetrating agent and combinations thereof. The biologically active substance, or alternately "active ingredient" does not have to be dissolved in a solvent but can be suspended or emulsified in a solvent. The donor solution or delivery medium can take the form of an aqueous or an organic liquid, a cream, a paste, a powder, a patch, or a mask, such as the tissue or non-tissue type of mask routinely used in spas, beauty salons, and other cosmetic installations.

Although not an exhaustive list, examples illustrating the term "mammal" include human, ape, monkey, rat, pig, dog, rabbit, cat, cow, horse, mouse, and goat. Skin surfaces or membranes according to the invention refer to those of a human or other mammal.

The term "viscous solution" refers to a solution that has an increased resistance to flow.

The term "cellular surface" refers to an outer layer of the skin or a cell membrane. Human skin is comprised of three layers: the epidermis or stratum corneum, the dermis and the hypodermis. The stratum corneum forms the outermost layer of the epidermis and consists of about 10 to about 20 layers of flattened, closely packed cells without nuclei having a thickness of about 10 to about 20 μm. The stratum corneum serves as a barrier to many substances and is selectively permeable to water and other compounds. On the other hand, the epidermis, having a thickness of about 50 to about 100 μm, comprises rapidly dividing basal cells that flatten as they move into the stratum corneum.

Finally, the innermost layer of skin, the dermis, comprises a matrix of various cells including collagen and other fibrous proteins and has a thickness of about 1 to about 3 mm. It is this layer that houses hair follicles, sebaceous glands and sweat glands. The term "transdermal" refers to the penetration and movement of a biologically active substance through the epidermis and dermis, or epidermis, dermis and hypodermis.

The term "transmembrane" refers to the penetration and movement of a biologically active substance from an extracellular environment to an intracellular environment.

The term "intradermal and/or intramembrane deposition" refers to the deposit of the biologically active substance within the stratum corneum, epidermis and/or the dermis of skin or within the various tissue layers or cell structures comprising a biological membrane. This definition is in contrast to "transdermal or transmembrane" that may include the passage of biologically active substances through the tissues into other underlying tissues thereby translocating beyond the tissues themselves.

The term "percutaneous penetration" refers to molecules that have by-passed the dermal blood supply and have diffused into tissue layers below the dermis. This may be useful for the various pharmaceutical applications of the subject system and methods.

The term "incoherent light" refers to electromagnetic waves that are unorganized and propagate with different phases. The term "pulsed incoherent light" is any incoherent light having a discrete ON and OFF period.

In contrast, "coherent light" refers to all light rays that are in phase and oriented in the exact same direction to produce a concentrated beam of light. Lasers generate these types of rays and can penetrate through materials such as solid media, including metals (e.g., sheet metal).

The term "light emitting diode (LED)" is a device that generally emits incoherent light when an electric voltage is applied across it. Most LEDs emit monochromatic light at a single wavelength that is out of phase with each other. According to the invention, most, if not all, types of LEDs can be used. For example, an LED having output range from red (approximately 700 nm) to blue-violet (approximately 350 nm) can be used. Similarly, infrared-emitting diodes (IRED) which emit infrared (IR) energy at 830 nm or longer can also be used.

"Optically clear medium" or "light pad" is a material that acts as a filter to all wavelengths except those wavelengths emitted from a light source. In a preferred embodiment, the light pad is comprised of clear poly(methyl methacrylate) or clear silicon rubber.

The term "reflective coating or layer" is a material that is coated on at least one surface of the light pad. Those skilled in the art will appreciate that the reflective layer can be a wavelength specific reflective coating (e.g., aluminum, ZnO, silver or any reflective paint).

The term "photokinetic" refers to a change in the rate of motion in response to light, as an increase or (blue part missing from EPO) decrease in motility with a change in illumination.

One embodiment of the invention relates to compositions for photokinetic transdermal and transmembrane delivery of a biologically active substance using preferably pulsed incoherent light or, alternatively, regulated coherent light. The composition may comprise a biologically active substance as the delivery medium.

The composition may alternatively comprise a biologically active substance and a solvent. The percent of biologically active substance in solvent can be in the range of between 0.0001 to 99.9999% (w/v). Preferably, the biologically active substance is present in a concentration range of between about 0.01% to about 2% (w/v). More preferably, the biologically active substance is present in a concentration range of between about 0.1 mg/ml to about 10 mg/ml in the solvent or, alternatively, between about 0.01% to about 1% (w/v). Due to the high level of permeation achieved by the methods and devices described herein, low concentrations of a biologically active substance in solvent or in other compositions described herein can be used for efficient transdermal or transmembrane delivery.

The composition may instead comprise a biologically active substance, a gelling agent and a solvent. The percent gelling agent in a solution of biologically active substance can vary depending on the type of gelling agent used. For example, Klucel is typically used at 1% (w/v), Natrasol at 1.5% (w/v), Carbopol at 0.75% (w/v), and hyaluronic acid is used in a concentration range of 0.25% to 2% (w/v) for, e.g., high molecular weight HA (and can be adjusted to even higher percentage for lower molecular weight HA if necessary).

Still further, the composition may comprise a biologically active substance, a photocatalytic agent and a solvent. Preferably, the photocatalytic agent has a band gap energy of between about 2.9 eV and about 3.2 eV and preferably is present in the composition at a concentration of between about 0.001% and 20% (w/w). More preferably, the photocatalytic agent is present in the composition at a concentration of 2% (w/w).

Finally, compositions according to the invention may comprise a biologically active substance, a gelling agent, a photocatalytic agent and a solvent. Preferably, the photocatalytic agent has a band gap energy of between about 2.9 eV and about 3.2 eV and preferably is present in the composition at a concentration of between about 0.001% and 20% (w/w). More preferably, the photocatalytic agent is present in the composition at a concentration of 2% (w/w). The biologically active substance preferably is present in the composition at a concentration of between about 0.01% and about 2% (w/v). The gelling agent preferably is present in the composition at a concentration of between 0.1% and 10% (w/v).

The biologically active substance of the above compositions may be selected from the group consisting of chemicals, cosmetics, drugs, antibiotics, peptides, hormones, proteins, DNA, RNA, various cosmetic active ingredients, and mixtures thereof.

The chemical may be a polar or non-polar compound. The polar compound may be selected from the group consisting of theophylline-7 acetic acid, sodium ascorbyl phosphate, ascorbic acid, ascorbyl palmitate, pyridoxine and nicotinic acid. For example, the polar compound may be pyridoxine. The non-polar compound may be selected from the group consisting of theobromine, theophylline, caffeine, and nicotinamide.

The drug may be selected from the group consisting of analgesics, anaesthetics, antacids, antianxiety drugs, antiarrhythmics, antibacterials, antibiotics, anticoagulants and thrombolytics, anticonvulsants, antidepressants, antidiarrheals, antiemetics, antifungals, antihistamines, antihypertensives, anti-inflammatories, antieoplastics, antipsychotics, antipyretics, antivirals, barbiturates, beta-blockers, bronchodilators, cold cures, corticosteroids, cough suppressants, cytotoxics, decongestants, diuretics, expectorants, hormones, hypoglycemics, immunosuppressives, laxatives, muscle relaxants, sedatives, sex hormones, sleeping drugs, tranquilizers, and vitamins. In one embodiment, the anaesthetic is lidocaine.

The compositions according to the invention may also comprise antibiotics as the biologically active substance. Antibiotics according to the invention are selected from the group consisting of amoxycillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, teracycline, coxycycline, chloramphenicol, and zithromycin. In one embodiment, the antibiotic is amphotericin B.

Similarly, in another embodiment of the invention, the biologically active substance is a peptide selected from the group consisting of glycine-tyrosine (Gly-Tyr), valine-tyrosine-valine (Val-Tyr-Val), tyrosine-glycine-glycine-phenylalanine-methionine (Tyr-Gly-Gly-Phe-Met) (SEQ ID NO: 1), tyrosine-glycine-glycine-phenylalanine-leucine (Tyr-Gly-Gly-PheLeu) (SEQ ID NO: 2), and aspartic acid-arginine-valine-tyrosine-isoleucine-histidine-proline-phenylalanine (Asp-Arg-Val-TYr-Ile-His-Pro-Phe) (SEQ ID NO: 3).

The hormone may be selected from the group consisting of methionine enkephalin acetate, leucine enkephalin, angiotensin II acetate, β-estradiol, methyl testosterone, progesterone, and insulin.

The protein may be selected from the group consisting of enzymes, non-enzymes, antibodies, and glycoproteins. In one embodiment of the invention, the protein is an enzyme.

Numerous biologically active substances useful in the cosmetic field/industry can also be delivered using the subject photokinetic intradermal delivery methods, optionally with the subject dermal patch. One category of cosmetically useful biologically active substance includes all skin components (such as collagen, natural or its synthetic forms) that could be readily replaced, replenished, or supplemented with exogenous molecules delivered by the subject methods. Merely to illustrate (and thus not limiting), the following categories of cosmetically beneficial molecules may be delivered using the subject methods: antioxidant-photoprotection molecules, such as Vitamin E (Tocopherols, in particular Alpha-tocopherol, and Tocotrienols), Ascorbate, Carotenoids (Beta-carotenoid-/Vitamin A, Lycopene, Zeaxantine, Lutein), Coenzyme Q (Ubiquinone, Idebenone), Glutathione (including Glutathion derivates: Ethyl ester, Cystine, etc.), Alpha-glycolic acid, SOD (Superoxide Dismutase), Catalase, Glutathione peroxydase, Reductase, Taurine, and Alpha-lipoic acid; polyphenols such as epsilon-viniferin, mixtures of resveratrol and epsilon-viniferin, and mixtures of polyphenolic, in particular stilbene and/or falvonol, oligomers and/or polymers; molecules with healing power, such as Melanin, Glycerol, peptides, or growth factors; Glycoproteins, such as Sialic acid (moisturizing action, infective prevention), GAGs (Chondroitin sulphate, Dermatan sulphate, Cheratan sulphate, Eparin, Eparan sulphate, Hyaluronates), Decorin; Collagene fibers-other fibers, such as Hydroxyproline (+Fe, +Vitamin C), Hydroxylysine, Glycine, Tropocollagen, Reticulin, Keratin, Elastin, MMPs (Matrix MetalloProteinases); beta-glucans; phytosterols; Anti-aging molecules, such as Arginine, Citrulline, Ceramides, Carnosine, Lysine, Inositol, Cysteine, Squalene, Squalane, Chitin, Sericine, peptides, or growth factors.

Compositions according to the invention can also contain a gelling agent in combination with the biologically active agent and solvent. The gelling agent may be selected from the group consisting of hydroxyethyl cellulose, hyaluronic acid, Natrasol®, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols, and tyloxapol. In one embodiment, the gelling agent is hydroxypropyl cellulose. In one embodiment, the gelling agent is hyaluronic acid.

Compositions according to the invention can also include a photocatalytic agent having a wide band gap energy. In one embodiment, the photocatalytic agent has a wide band gap of between about 2.9 eV and about 3.2 eV. In a preferred embodiment, the photocatalytic agent is a rutile form of titanium dioxide ($TiO_2$). In another embodiment, the photocatalytic agent is an anatase form of $TiO_2$, brookite form of $TiO_2$, ZnO, $ZrO_2$ and $Sc_2O_3$.

The composition may also comprise a solvent that is an aqueous or organic solvent. In one embodiment, the aqueous solvent is water. In yet another embodiment, the aqueous solvent is an aqueous solution of ethyl lactate or propylene glycol. The water may be HPLC grade or purified by means such as reverse osmosis or distillation.

The donor solution or delivery medium according to the invention is comprised of a biologically active substance itself or any mixture of a biologically active substance with a solvent, a gelling agent, a photocatalytic agent, a carrier or adjuvant, a skin-penetrating agent, emulsifier, one or more different biologically active substances, polymers, excipients, coatings and/or combinations thereof. In essence, the biologically active substance or substances can be combined with any combination of pharmaceutically acceptable components to be delivered to the cellular surface by the method described herein, e.g., photokinetic transdermal and transmembrane delivery. The biologically active substance does not have to be dissolved in a solvent but can be suspended or emulsified in a solvent. The donor solution or delivery medium can take the form of an aqueous or an organic liquid, a cream, a paste, a powder, or a patch. The donor solution can also comprise microspheres or nanospheres of biologically active substances.

The invention described herein is particularly useful for transdermal delivery of compounds containing chromophores. Without being bound by any particular theory, it is believed that the molecular chromophore absorbs photon energy and/or the energy from an excited photocatalytic agent. As the chromophore returns to ground state, it generates kinetic energy. With each pulse of incoherent light, the chromophore's vibration will incrementally clear a pathway through the skin.

Consistent with this theory, chemical and heat energy can cause molecular shape changes and increases in Brownian motion within a system. These energies cannot be easily cycled and are not directional. Light energy, on the other hand, is readily defined by wavelength and can be easily controlled for cycle time stimulation and incident direction. Molecular conformational changes as a result of optical stimulation is a widely known phenomenon exhibited by many classes of compounds with degrees of shape change determined by the individual molecular structure. The conformational changes initiated by the exemplary photokinetic method are reversible; the molecules tend to revert to a resting state as the optical energy is dissipated during the OFF part of the cycle. Thus, cyclic light stimulation creates a repeated and reversible molecule shape change or gross physical movement on a molecular scale.

In addition, according to Le Chatelier's principle, if a system in chemical equilibrium is subjected to a disturbance, it tends to change in a way that opposes this disturbance. Molecular systems move in the direction to reduce the external stimuli; molecules tend to move away from an energy source. Kausar et al (Photocontrolled translational motion of a microscale solid object on azobenzene-doped liquid-crystalline films. Angew Chem Int Ed Engl. 48(12): 2144-79, 121, 2009) have published a paper detailing how a molecule can be translocated around a surface as a response to light stimulation, generally by moving away from the light energy. In the photokinetic system, the drug is applied to the tissue surface and illuminated from a direction opposite the tissue. If the molecule is to escape the light energy stimulation, then it moves in a direction away from the stimulation and into the tissue. The repeated cycling of the molecular shape adds a gross movement aspect to the system much like sand going through a vibrating sieve. The possible interaction of cycled incident incoherent light on the skin itself may also cycle the tissue structure and transdermal pathways. These cycled membrane changes may impart a pumping action on the pathways through the tissue much like a sieve with cycled pore sizes furthering the sand/sieve analogy.

Similarly, the invention described herein is also useful for transmembrane delivery of biologically active substances. For example, a person of skill in the art could inject a therapeutically effective pharmaceutical substance, such as a chemotherapeutic agent, next to a solid tumor mass. An LED that is embedded or held next to the tumor mass can be used to deliver the therapeutic substance from the extracellular environment to the intracellular environment, effectively causing apoptosis in the targeted area.

In addition to compositions, the invention also provides methods of photokinetic delivery of biologically active substances using pulsed incoherent light. One method includes preparing a solution comprising a biologically active substance and a solvent, applying the solution to a cellular surface, illuminating the solution on the cellular surface with a pulsed incoherent light having a selected wavelength, pulse rate and duty cycle and allowing the solution to permeate the cellular surface. In another embodiment, the method includes preparing a solution comprising a biologically active substance, a solvent and a gelling agent, applying the solution to a cellular surface, illuminating the solution on the cellular surface with a pulsed incoherent light having a selected wavelength, pulse rate and duty cycle and allowing the solution to permeate the cellular surface. In yet another embodiment, the method includes preparing a solution comprising a biologically active substance, a solvent, a gelling agent and a photocatalytic agent, applying the solution to a cellular surface, illuminating the solution on the cellular surface with a pulsed incoherent light having a selected wavelength, pulse rate and duty cycle and allowing the solution to permeate the cellular surface. In a preferred embodiment, the cellular surface is an outer layer of a skin of a mammal or a cell membrane.

3. Illustrative Photokinetic Devices

FIG. 1 illustrates testing device 100 in accordance with the invention. Testing device 100 provides photokinetic transdermal and transmembrane delivery of biologically active substances to a portion of skin or membrane by illuminating the biologically active substance with pulsed incoherent light. Testing device 100 includes a light source 3 that illuminates a biologically active substance in donor cell 4 such that the biologically active substance diffuses into skin 6 with little to no damage to skin 6. Testing device 100 can also be arranged such that the light source 3 illuminating a biologically active substance in donor cell 4 is parallel to a surface on which it is mounted.

Testing device 100 preferably includes a driver circuit 2 that provides control signals to light source 3 such that pulsed incoherent light is provided to donor cell 4. Driver circuit 2 may also provide control signals that control the intensity, direction, and/or frequency of light source 3. A pulsed incoherent light may advantageously reduce damage to skin 6 as compared to a continuous light source, and provides photokinetic transdermal and transmembrane delivery of biologically active substances within donor cell 4 to skin 6.

Driver circuit 2 may regulate an electrical signal that turns (i.e., switches) light source 3 ON and OFF at a particular frequency. Such an electrical signal may be provided, for example, by a voltage generator. Alternatively, driver circuit 2 may itself be a voltage generator and may produce an electrical signal to control the switching characteristics of light source 3. For example, a voltage generator coupled to light source 3 may provide a square wave to power light source 3. This square wave may have a desired period such that light source 3 provides incoherent light with a desired frequency (e.g., a square wave period of 0.5 seconds would cause light source 3 to switch at 2 Hz).

Light source 3 preferably provides incoherent light (to avoid any potential damage done to skin 6 during the use of testing device 100). Light source 3 may be, for example, an LED, halogen light source, fluorescent light source, natural light, or other source of light. More particularly, light source 3 can be a light emitting diode (LED) (fluorescence, 350-1700 nm) or an infrared light emitting diode (ILED) or a Mercury-Argon (253-922 nm), pulsed xenon (UV-VIS, 200-1000 nm), deuterium (UV, 200-400 nm), deuterium/halogen (UV/VIS/NIR, 200-1700 nm) or tungsten halogen (color/VIS/NIR, 360-1700 nm) light source. Light source 3 preferably is operable in the range from red (approximately 700 nm) to blue-violet (approximately 350 nm). Similarly, infrared-emitting diodes (IREDs) that emit infrared energy at 830 nm or longer may be used.

Light source 3 does not have to be an incoherent light source. Alternatively, light source 3 may be a coherent light source such as, for example, a laser. In that case, driver circuit 2, or other regulation circuitry, is preferably used to turn a coherent light source 3 ON and OFF to reduce the amount of damage to skin 6 while still photokinetically delivering a biologically active substance to donor cell 4. Furthermore, a light regulation/conversion device may be placed between a coherent light source 3 and donor cell 4 to convert the coherent light to incoherent light.

Note that a device such as driver circuit 2 or a controlled voltage generator is not required to pulse light source 3. Alternatively, shutter 11 may be employed between light source 3 and donor cell 4. Such a shutter selectively OPENs and CLOSEs such that donor cell 4 is supplied pulsed incoherent light from light source 3. The speed at which the shutter OPENs and CLOSEs determines the frequency of the light pulsed onto the skin. Filters (not shown) may also be placed between light source 3 and donor cell 4 in order to remove, for example, light of specific wavelengths that may damage skin 6. Alternatively, light source 3 may be immersed in a solution found in donor cell 4. Preferably, the wavelength of light reaching skin 6 is chosen not only to reduce damage to skin 6, but also to increase the photokinetic activity in donor cell 4 (e.g., 350 nm to 450 nm). The pulse rate of such light may also be between 1.7 cps and 120 cps (e.g., 24 cps). If fluorescent light is employed as light source 3, it preferably has a wavelength range from about 260 nm to about 760 nm. If ultraviolet, visible, near infrared, or halogen light is employed as light source 3, the light source preferably has a wavelength range from about 340 nm to about 900 nm. The invention, however, is not limited to the these wavelengths.

Donor cell 4 holds a biologically active substance (e.g., chemicals, drugs, antibiotics, peptides, hormones, proteins, DNA, RNA and mixtures thereof). Donor cell 4 may also include a solvent that forms a solution with the biologically active substance. The solution may also include a photocatalytic (having, for example, a band gap energy of between about 2.9 eV and about 3.2 eV) and/or a gelling agent. The solvent may be an aqueous or an organic solvent. Furthermore, skin 6 may be a cellular surface which is an outer layer of a skin. Generally, skin 6 may be any medium that allows at least the biologically active portion of donor cell 4 to diffuse into that medium in response to that medium being exposed to light source 3. In one embodiment, this medium is a cell membrane for transmembrane delivery.

Clamp 5 is preferably included in testing device 100 to couple donor cell 4 and skin 6 to receiving cell 7. Receiving cell 7 may be present in container 17 as a result of diffusion of at least the biologically active portion of donor cell 4 through skin 6. Also, receiving cell 7 may contain a solvent, e.g., HPLC grade water, wherein diffusion of at least the biologically active portion of donor cell 4 through skin 6 enters into the solvent. Generally, the concentration of the biologically active substance is higher in donor cell 4 than in receiving cell 7. Skin supports 16 may also be included in order to position skin 6 above container 17 and below light source 3. Donor cell 4 is located in container 14 and preferably contacts an area of skin 6. Container 14 and container 17 may be the same container. Furthermore, a skin aperture (not shown) may exist to receive at least a portion of skin 6 such that skin 6 separates container 14 from container 17.

Temperature control device 8 is preferably applied to at least a portion of container 7. Temperature directors 18 may be included as a part of container 17 or coupled to container 17 to direct temperature control device 8. Temperature directors 18 may also be used to structurally provide support for a heat source such as a heat bath. For example, hot water may be placed in housing defined by temperature directors 18 and a portion of container 17 between temperature directors 18. Further to this example, a heat source may be used to heat such water. Alternatively, a heat source may be directly coupled to container 17. Preferably, temperature control device 8 heats container 17 to a constant level. While the temperature of the solvent in receiving cell 7 can vary, it is preferably about 37° C., human body temperature, or about 33.5° C., human skin surface temperature. For applications requiring container 17 to be cooled, temperature control device 8 may additionally or alternatively be a cooling source. A temperature sensor (not shown) may be placed in, on, or about container 17 or a heat source such that temperature control device 8 keeps container 17 at a particular temperature for a particular period of time.

Stir bar 9 may be included in container 17 to stir any solution in container 17. Preferably, stir bar 9 constantly stirs the solution in container 17. Container 17 may be alternatively stirred, for example, by a shaking device. Removal of stir bar 9 would, for example, allow container 17 to be easily sanitized while reducing the design complexity of container 17. Stir bar 9 may be connected to an electrical motor (not shown).

Port 10 may be included in container 17 to add or remove samples to or from receiving cell 7 or solutions to or from container 17. Generally, port 10 is an aperture in container 17. Guide tube 12 may form an extended port 10 such that a sample recovery or dispersal tool can easily migrate to port 10. Cover 13 may be employed on port 10 (or guide tube 12) such that contaminants from outside container 17 do not pass through port 10 when samples are being added or removed from container 17. Guide tube 12 is generally an adapter. For example, if the recovery/dispersal tool is a needle, then guide tube 10 preferably facilitates the coupling of the needle to port 10.

Lens 23 may be included in testing device 100 to, for example, focus light source 3 on donor cell 4 or to provide a transparent medium in which light from light source 3 may pass onto donor cell 4 while contaminants from outside container 14 are isolated from donor cell 4. Lens 23 may be a transparent medium, such as, for example, a transparent polymer or glass.

Container 17 may include insulation 15 to control the amount of heat supplied to container 17. Insulation 15 may also be part of a heat bath and may be filled with water. The amount of insulation 15 about temperature control device 8 may be reduced such that temperature control device 8 affects the temperature of container 17 more than ambient heat.

Figure 2:
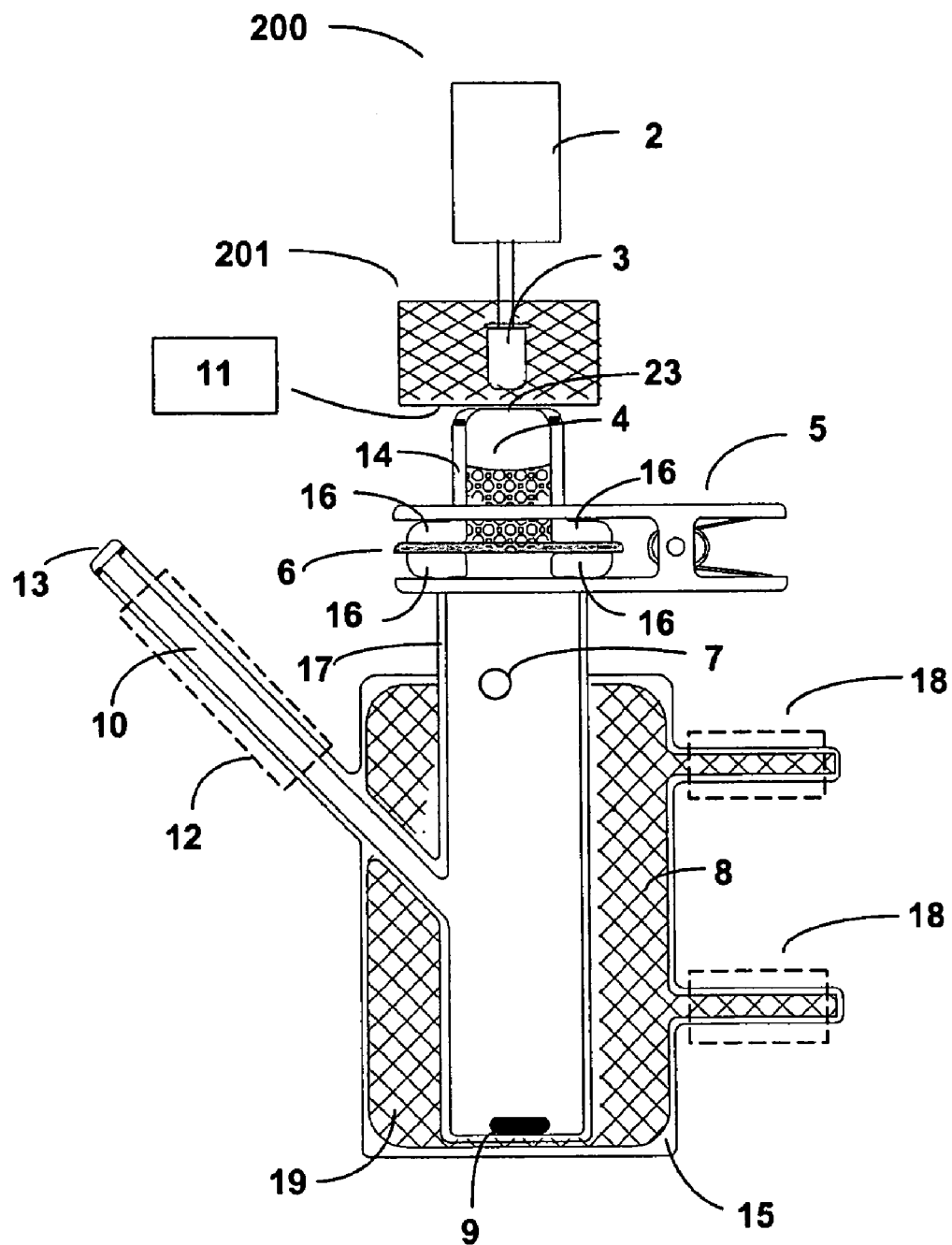
FIG. 2 shows a Franz skin diffusion device similar to that in FIG. 1 except the light source is embedded in an optically clear medium or light pad that does not absorb the wavelength emitted from the light source.

FIG. 2 illustrates testing device 200 in accordance with the invention. Testing device 200 includes light pad 201 and is otherwise similar/identical to testing device 100 of FIG. 1. Light pad 201 includes at least one and preferably more than one light source 3, which is preferably an LED. Light pad 201 is preferably fabricated from an optically clear material (e.g., poly (methyl methacrylate) or silicone rubber). Similar to testing device 100, testing device 200 can also be oriented differently than shown.

Figure 3A:
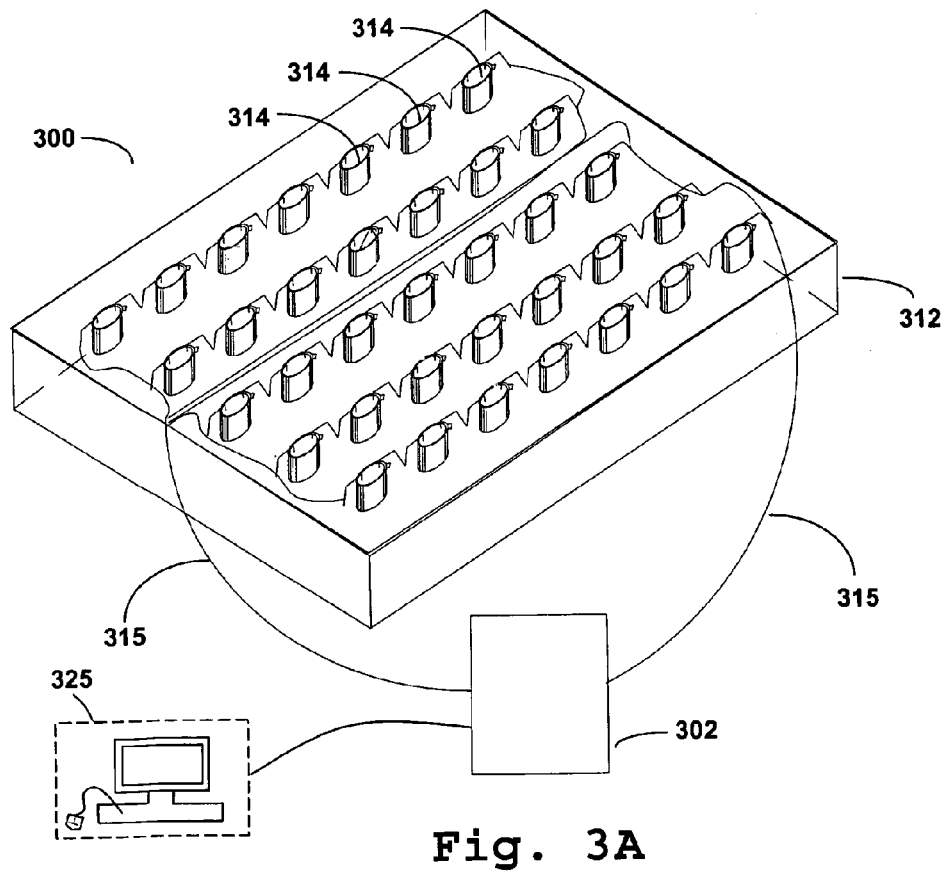
FIG. 3A shows an array of light sources embedded in an optically clear medium or light pad and electrically coupled to each other and to a control device or power supply.

FIG. 3A illustrates light pad 300 in accordance with the invention. Light pad 300 includes driver circuit 302, base 312, light source 314, and wiring 315. Wiring 315 may be included to electrically couple control device 302 (or a power supply) to one or more light sources 314, and wiring 315 may have a protective sheath. Base 312 is preferably a silicon substrate in which light sources 314 are fabricated. Light sources 314 are preferably incoherent sources of light and are preferably LEDs having a narrow bandwidth. Alternatively, other types of light sources may be used. Light sources 314 may be turned ON and OFF by driver circuit 302 either as a group, individually, or in sections. For example, light sources 314 may be arranged as multiple arrays of light sources. Driver circuit 302 may then selectively pulse only a single array of light sources 314 such that only a desired portion of a medium (e.g., skin 6 from FIGS. 1 and 2) receives pulsed light. Moreover, multiple arrays can be included on light pad 300 in which each array includes LEDs of a specific wavelength. Thus, when only a specific wavelength is desired or needed, driver circuit 302 can selectively turn ON the array comprised of LEDs having that particular wavelength. For example, light pad 300 may include an array of ILEDs and an array of LEDs where driver circuit 302 selectively switches between the ILED array and the LED array. This may be desirable when a biologically active substance is more reactive to or less degraded/denatured by light of a particular wavelength.

Instead of having arrays of particular wavelengths, other characteristics may be utilized. For example, two arrays may have LEDs of the same wavelength (or different wavelengths), and the arrays may be of different intensities or may focus light in different directions. Light sources 314 may be mounted on gears (not shown) that can be turned/rotated by motors (not shown) and controlled by driver circuit 302 such that the direction and intensity of light being provided to a particular area can be manipulated. Driver circuit 302 may be controlled by computer 325 either directly or via a graphical user interface (GUI).

Light pad 300 can be, for example, a tanning bed. If light pad 300 provided coherent light, a light scatter device, filter, or conversion device can be provided to convert the coherent light into incoherent light.

Figure 3B:
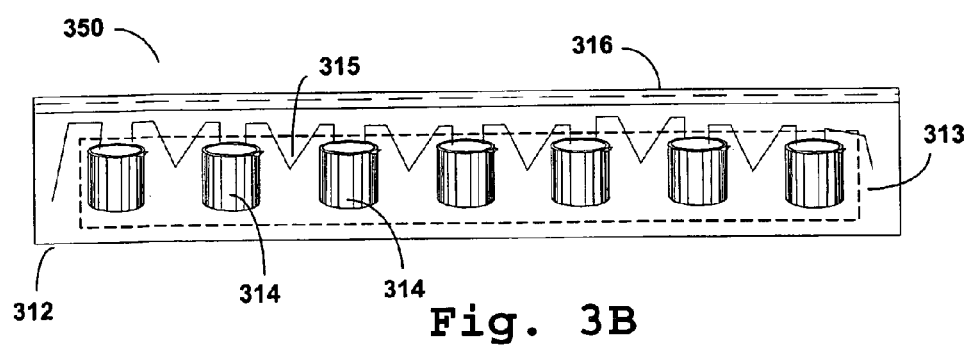
FIG. 3B illustrates multiple light sources electrically connected in series and embedded in an optically clear medium or light pad wherein the upper surface of the light pad is coated with a reflective layer and the lower surface of the light pad is optically clear.

FIG. 3B illustrates light array 313 mounted in base 312. Array 313 includes two or more light sources 314 electrically connected in series by wiring 315. If light sources 314 are to provide light below base 312, reflective layer 316 may be included above base 312 to reflect light scattered from base material or skin while base 312 remains a transparent medium. Multiple light sources 314 may have different wavelengths such that light sources 314 having a particular wavelength may be selectively turned ON and OFF to provide light of a single selected wavelength or multiple selected wavelengths. Light sources 314 may provide light above base 312. In this case, reflective layer 316 may be placed on base 312 (which does not have to be transparent) and beneath light sources 314 to reflect light above base 312. The reflective layer can be a wavelength specific reflective coating (e.g., aluminum, ZnO, silver or any reflective paint).

The in vitro and in vivo methods and devices of the invention can also be used in combination with other active delivery techniques such as ionotophoresis, sonophoresis, phonophoresis, or used in conjunction with microporation methods such as microneedles, electroporation, phonophoresis, laser poration/obliteration.

A more detailed description of an exemplary embodiment of the photokinetic device—a Franz cell apparatus, is provided below.

Franz Permeation Cell In Vitro Method

A traditional Franz cell apparatus (PermeGear, Inc, Bethlehem Pa.) was modified to allow placement of the LEDs into the donor chamber. The tissue area exposed to drug was 1 cm$^2$. The cells were placed in an aluminum block equipped with magnetic stirrer and maintained at constant temperature. Target tissue (intact human split thickness skin) was placed between the donor and recipient chamber and clamped together to create a seal. Drugs were formulated in appropriate carriers and placed in the donor chamber. In the recipient chamber, either HPLC grade water or buffer was used for ease of analysis. Samples from the recipient chamber fluid are taken through the side port at various time points. Control "passive permeation" cells were set up the same way, without the LEDs.

LEDs of discrete wavelengths were purchased from Roithner Lasertechnick GmbH, Vienna, Austria, but other equivalent LEDs may also be suitable. LEDs used are specified as peak emitting wavelength value in nanometers (nm)±spectrum ½ width in nanometers at 50% relative radiant intensity output along with specified radiated output power in milliwatts (mW) and manufacturers product number: 350 nm±5 nm 200 µW (RLT350-30), 370 nm±5 nm 1.2 mW (RCL-370-10), 390 nm±5 nm 8.1 mW (LC503MUV1), 405 nm±5 nm 10 mW (LED405-03V), 436 nm±10 nm 12 mW (LED436-03), and 450 nm±10 nm 20 mW (LED450-06).

An adjustable pulse rate square wave signal generator constructed by the inventors providing an equal time ON and OFF cycle (or 50% duty cycle) was used to drive LEDs. Driver output pulse frequency is specified as the number of complete ON-OFF cycles per second (cps), i.e., 24 complete ON-OFF cycles in one second is specified as 24 cps. The LEDs were driven at or below manufacturer's specified current by incorporating current limiting resistors in the drive circuits. Current limiting resistors were selected based on the formula: resistor value in ohms=(pulse generator supply voltage−LED specified voltage)/LED specified current rating (in amperes). Resistors selected were equal to or greater than the formula determined value in order to prevent excessive radiant heat generation from the LEDs.

The subject tissue is placed between the donor chambers and recipient chambers and held together by a clamp (not shown) providing sealed separation between the two chambers. The recipient chamber is filled with distilled water through the sidearm sampling port. The donor chamber holds the subject drug dissolved in an acceptable drug carrier formulation. At various time points, samples are dawn from the side arm port for chemical analysis. Control cells are set up with the same conditions as the photokinetic cells, but without the LED.

The photokinetic Franz cell testing portion includes an electrical driver circuit (not shown) that provides control signals to the LED light source. The electronic driver circuit regulates an electrical signal that turns (i.e., switches) light source ON and OFF at a particular selected frequency. The electrical drive current is limited to proved current levels at or below the LED's specified current to eliminate exogenous heat generation from the LED. The voltage generator coupled to light source provides an electrical square wave to power the light source. This square wave has a desired ON and OFF period such that light source provides pulsed incoherent light from the LED source with a desired pulse frequency (e.g., a square wave 50% duty cycle period of 0.5 seconds ON and a 0.5 seconds OFF would cause light source to switch at 1 Hz or 1 cycle per second (CPS)). Pulsed light frequency used herein range from 24 to 100CPS as reported. Useful ranges of pulse rate may exceed those reported herein. The preferred embodiment has a range of 1 to 120 CPS.

Furthermore, the proportion of ON time vs. OFF time 50% duty cycle or equal ON:OFF time was determined out of convenience for the electronic control construction and is not intended to limit the specifications of the invention. In general, the excitation time required for molecular stimulation can be quite short, while the time required to dissipate this energy may be longer. A shorter period of ON time vs. OFF time, for example an ON time of 10% with an OFF time of 90% of the total cycle time, may also be useful for the invention. This may impact the pulse rate frequency determination, which may then affect the attainable flux rate. An added advantage of shorter ON time (lower percentage duty cycles) is that in a battery operated system, this would conserve energy. Thus in certain embodiments, there is a period ON and OFF illumination times to provide a cyclical period of light stimulation with a period of OFF resting time. A discrete ON time and a discreet OFF time, in the range of for example 1% ON/99% OFF to 99% ON to 1% OFF (including any integer values in between, such as 2%ON98%OFF, 5%ON95%OFF, 10%ON90%OFF, 15%ON85%OFF, etc.) are all contemplated embodiments of the invention, with 50%ON50%OFF being preferred in certain situations.

Figure 4:
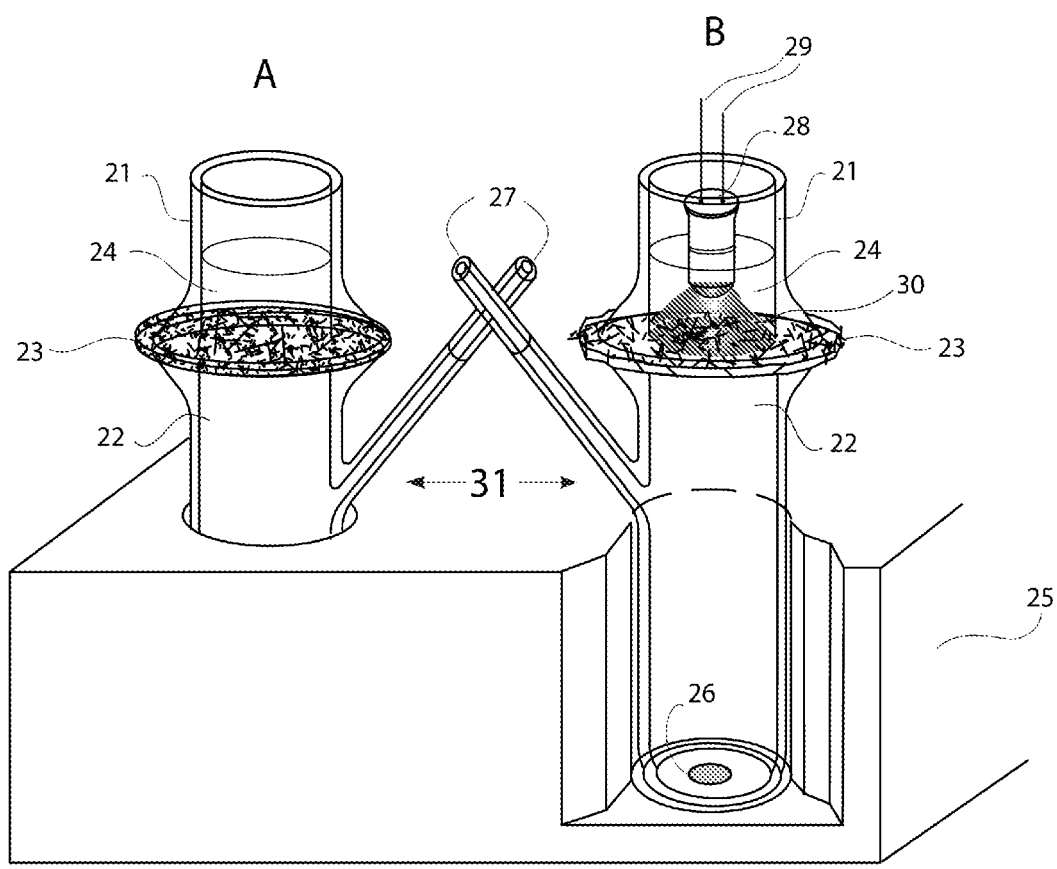
FIG. 4 illustrates exemplary Franz diffusion cell apparatus for in vitro determination of photokinetic conditions of light wavelength and pulse rate.

FIG. 4 illustrates an exemplary Franz diffusion cell apparatus for in vitro determination of photokinetic conditions of light wavelength and pulse rate, in accordance with the present disclosure. Franz diffusion cells 31 are shown within a heat block 25, one (B) being shown in partial cut-away for purposes of clarity. Skin tissues 23 are inspected under six times magnification for holes or tears or other imperfections. Skin 23 is placed and floated onto the donor chamber containing recipient fluid in a method to prevent air bubbles between the recipient fluid and the skin. The donor chamber 21 is then affixed and held in place by a clamp (not shown) so that the skin separates the two Franz cell chambers, donor chamber 21 and recipient chamber 22. Skin placement is oriented to mimic an in vivo situation with the dermal skin surface facing the recipient chamber 22 and the epidermal/stratum corneum surface facing the donor chamber 21.

The testing device illustrated in FIG. 4, in accordance with the present disclosure, provides photokinetic transdermal and intradermal delivery of biologically active substances to a portion of skin by illuminating a biologically active substance with pulsed incoherent light. Testing device can include a light source (not shown) that illuminates a biologically active substance in donor chamber 21 such that the biologically active substance diffuses into the skin tissue 23 without damage to the skin tissue 23. Testing device can also be arranged such that the light source illuminating a biologically active substance in donor chamber 21 is horizontal or parallel to a surface on which it is mounted.

Testing device may include an electrical driver circuit that provides control signals to the light source such that pulsed incoherent light is provided to the donor chamber 21. The driver circuit may also provide control signals that control the intensity, direction, and/or frequency of the light source. A pulsed incoherent light advantageously and cyclically illuminates the subject drug formulation 24 producing a period of excitation and relaxation of the drug 24 and the skin tissue 23 which provides photokinetic transdermal translocation of biologically active substances within donor chamber 21 into and through the skin tissue 23.

Electronic Driver circuit may regulate an electrical signal that turns (i.e., switches) light source ON and OFF at a particular frequency. Such an electrical signal may be provided, for example, by a voltage generator controlled by an electronic flasher circuit. Alternatively, a driver circuit may itself be a voltage generator and may produce an electrical signal to control the switching characteristics of light source. For example, a voltage generator coupled to light source may provide an electrical square wave to power the light source. This square wave may have a desired ON and OFF period such that light source provides pulsed incoherent light with a desired pulse frequency (e.g., a square wave period of 0.5 seconds ON and a 0.5 seconds OFF would cause light source to switch at 1 Hz or 1 cycle per second (CPS)).

The light source preferably provides incoherent light (to avoid any potential damage done to skin 23 or cause damage to the drug or cosmetic active ingredient 24 during the use of testing device). The light source may be, for example, an LED, halogen light source, fluorescent light source, natural light, or other source of light. More particularly, the light source can be a light emitting diode (LED) (fluorescence, 350-1700 nm) or an infrared light emitting diode (ILED) or a Mercury-Argon (253-922 nm), pulsed xenon (UV-VIS, 200-1000 nm), deuterium (UV, 200-400 nm), deuterium/halogen (UV/VIS/NIR, 200-1700 nm) or tungsten halogen (color/VIS/NIR, 360-1700 nm) light source. The light source preferably is operable in the range from red (approximately 700 nm) to blue-violet (approximately 350 nm). Similarly, infrared-emitting diodes (IREDs) that emit infrared energy at 830 nm or longer may be used.

The light source does not have to be an incoherent light source. In accordance with aspects of the present disclosure, the light source may be a coherent light source such as, for example, a laser. In that case, the driver circuit, or other regulation circuitry, is preferably used to turn the coherent light source ON and OFF to reduce the amount of damage to skin tissue 23 while still photokinetically delivering a biologically active substance 24 from the donor cell 21 into the eye tissue 23. Furthermore, a light regulation/conversion device may be placed between a coherent light source in the donor cell 21 to convert the coherent light to incoherent light.

Note that a device such as an electronic driver circuit or a controlled voltage generator is not required to pulse light source. Alternatively, a mechanical shutter may be employed between light source and donor cell. Such a shutter selectively OPENs and CLOSEs such that donor cell is supplied pulsed incoherent light from light source. The speed at which the shutter OPENs and CLOSEs determines the frequency of the light pulsed onto the eye tissue. Filters (not shown) may also be placed between light source and the donor cell in order to remove, for example, light of specific wavelengths that may damage the skin or reduce photokinetic activity. Alternatively, the light source may not need be immersed or optically coupled with the drug solution found in donor cell. The essential arrangement is when a drug in contact with the subject's skin is positioned to receive pulsed incoherent light from a selected source at a selected pulse frequency.

The wavelength of light reaching eye tissue may be chosen not only to reduce damage to the tissue, but also to increase the photokinetic activity in donor cell (e.g., 350 nm to 450 nm). The pulse rate of such light may also be between 1.7 cycles per second (cps) and 120 cps (e.g., 24 cps). If fluorescent light is employed as light source, it may have a wavelength range from about 260 nm to about 760 nm. If ultraviolet, visible, near infrared, or halogen light is employed as light source, the light source may have a wavelength range from about 340 nm to about 900 nm. The invention, however, is not limited to these wavelengths. Any method to pulse illuminate the drug that is in contact with the eye tissue may provide the photokinetic transdermal drug delivery.

Donor chamber 21 holds a biologically active substance (e.g., chemicals, drugs, antibiotics, peptides, hormones, proteins, DNA, RNA and mixtures thereof). Donor chamber 21 may also include a solvent that forms a solution with the biologically active substance. The solution may also include a gelling agent, as appropriate. The solvent may be an aqueous or an organic solvent. Generally, skin tissue 23 may be any medium that allows at least the biologically active portion drug formulation 24 contained in the donor chamber 21 to diffuse into that medium in response to that medium being exposed to a selected light source pulsed at a selected pulse rate. In one embodiment, this medium is a skin for transdermal delivery. In another embodiment the medium is skin tissue for intradermal delivery.

A clamp (not shown) may optionally be included in testing device to couple donor chamber 21 and skin tissue 23 to the recipient chamber 22. Drug components comprising the donor formulation 24 placed in donor chamber 21 may be present in recipient chamber 22 as a result of the diffusion of at least the biologically active portion 24 of donor chamber 21 through eye tissue 23. Also, recipient chamber 22 may contain a solvent, e.g., HPLC grade water, wherein diffusion of at least the biologically active portion 24 of donor cell 21 through eye tissue 23 enters into the solvent. Generally, the concentration of the biologically active substance is higher in donor chamber 21 than in recipient chamber 22.

Temperature control device 25, such as a heat block, is preferably applied to at least a portion of the recipient chamber 22. Temperature directors may be included as a part of heat block 25 or coupled to the recipient chamber 22 to direct temperature control device 25. Temperature directors (not shown) may also be used to structurally provide support for a heat source such as a heat bath. For example, warm water may be placed in housing defined by temperature directors and a portion of recipient chamber 22 between temperature directors. Further to this example, a heat source may be used to heat such water. Alternatively, a heat source may be directly coupled to recipient chamber 22. Preferably, temperature control device 25 heats the Franz cell assembly 31 to a constant level. While the temperature of the solvent in recipient chamber 22 can vary, it is preferably about 37° C., human body temperature, or about 35.5° C., human skin surface temperature. For applications requiring Franz cell assembly 31 to be cooled, temperature control device 25 may additionally or alternatively be a cooling source. A temperature sensor (not shown) may be placed in, on, or about the Franz cell 31 or a heat source such that temperature control device 25 keeps the Franz cell 31 at a particular temperature for a particular period of time.

With continued reference to FIG. 4, stir bar 26 may be included in recipient chamber 22 to stir any solution in recipient chamber 22. Preferably, stir bar 26 constantly stirs the solution in recipient chamber 22. Recipient chamber 22 may be alternatively stirred, for example, by a shaking device. Removal of stir bar 26 would, for example, recipient chamber 22 to be easily sanitized while reducing the design complexity of recipient chamber 22 assembly. Stir bar 26 may be connected to an electrical motor (not shown).

Side arm port 27 may be included in recipient chamber 22 to remove samples from and to replace sample volume into recipient chamber 22 or solutions to or from recipient chamber 22. Generally, port 27 is an aperture into recipient chamber 22. An alternate guide tube (not shown) may be included to form an extended port 27 such that a sample recovery or dispersal tool can easily migrate to port 27. A cover may be employed on port 27 such that contaminants from outside recipient chamber 22 do not pass through port 27 when samples are being added or removed from recipient chamber 22. In accordance with certain aspects of the present disclosure, if a guide tube is included in association with port 27, the guide tube is generally an adapter. For example, if the recovery/dispersal tool is a needle, then guide tube 27 preferably facilitates the coupling of the needle to port 27.

The Franz cell apparatuses 31 are designated to determine passive permeation A or photokinetic permeation B into and through skin tissues 23. The Franz cell has two chambers— the donor chamber 21 and the recipient chamber 22. Skin tissue 23 is placed between the two chambers and sealed into place and held between the two chambers by a clamp (not shown). The recipient chamber 22 is filled with an aqueous solution selected to allow for chemical analytical methods. The donor chamber 21 is filled with a drug in a pharmacologically acceptable formulation, as described herein. The recipient chamber 22 is constantly stirred by a magnetic stir bar 26. A portion of the recipient chamber is placed in a heat block 25 heated to a physiological temperature (about 35.5° C.). At various time points, samples are dawn from the side arm port 27 for purposes of chemical analysis.

The passive permeation cell A provides permeation flux rates though the skin tissue. In the photokinetic Franz cell B, a selected LED 28 is partially submerged within the drug formulation 24 within the donor chamber 21. The LED is driven by an external pulse generator at a selected pulse rate and connected to the LED electrical connectors 29. The skin tissue 23 is positioned in contact with and under the drug formulation 24. The drug formulation in contact with the tissue is illuminated by the light 30 generated by the LED 28.

By sampling the fluid from the recipient cells 22 and performing chemical analysis, comparisons of the two permeation conditions: A passive transdermal permeation and B photokinetic transdermal permeation can be determined.

Figure 5:
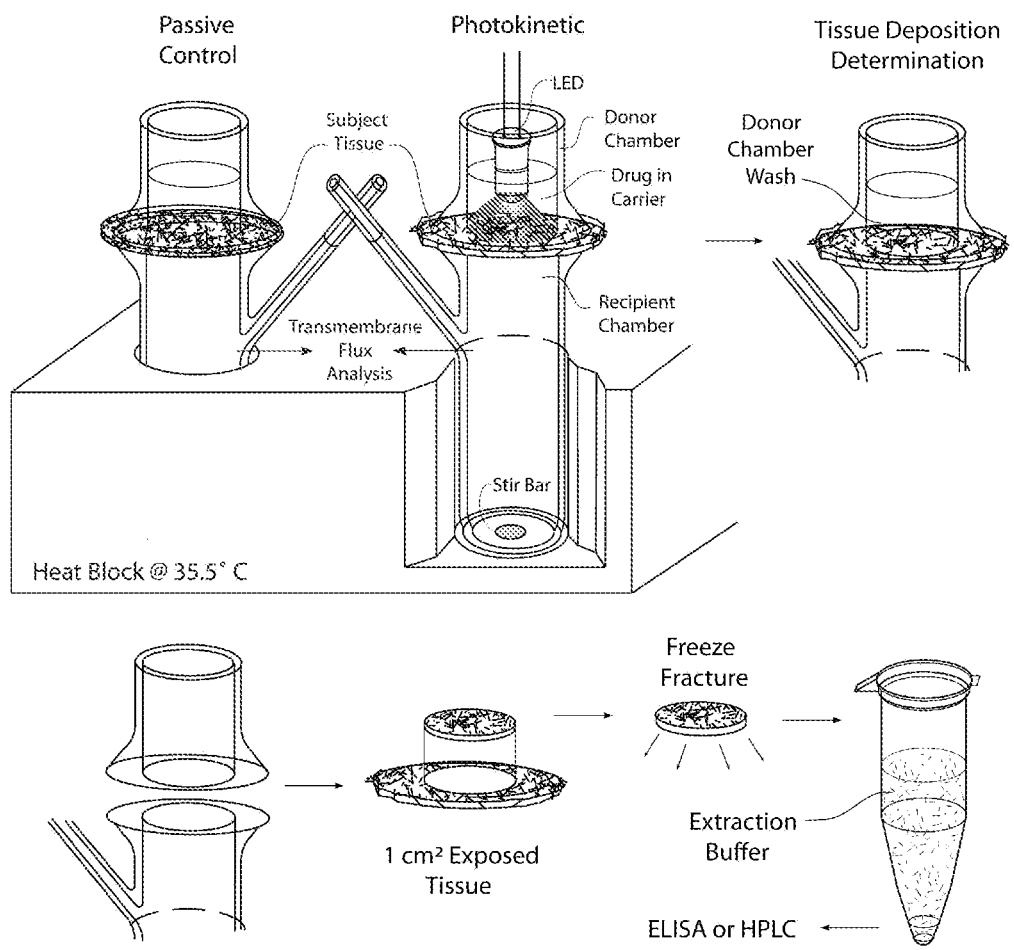
FIG. 5 is a schematic drawing showing determination of intradermal drug concentration.
Figure 6:
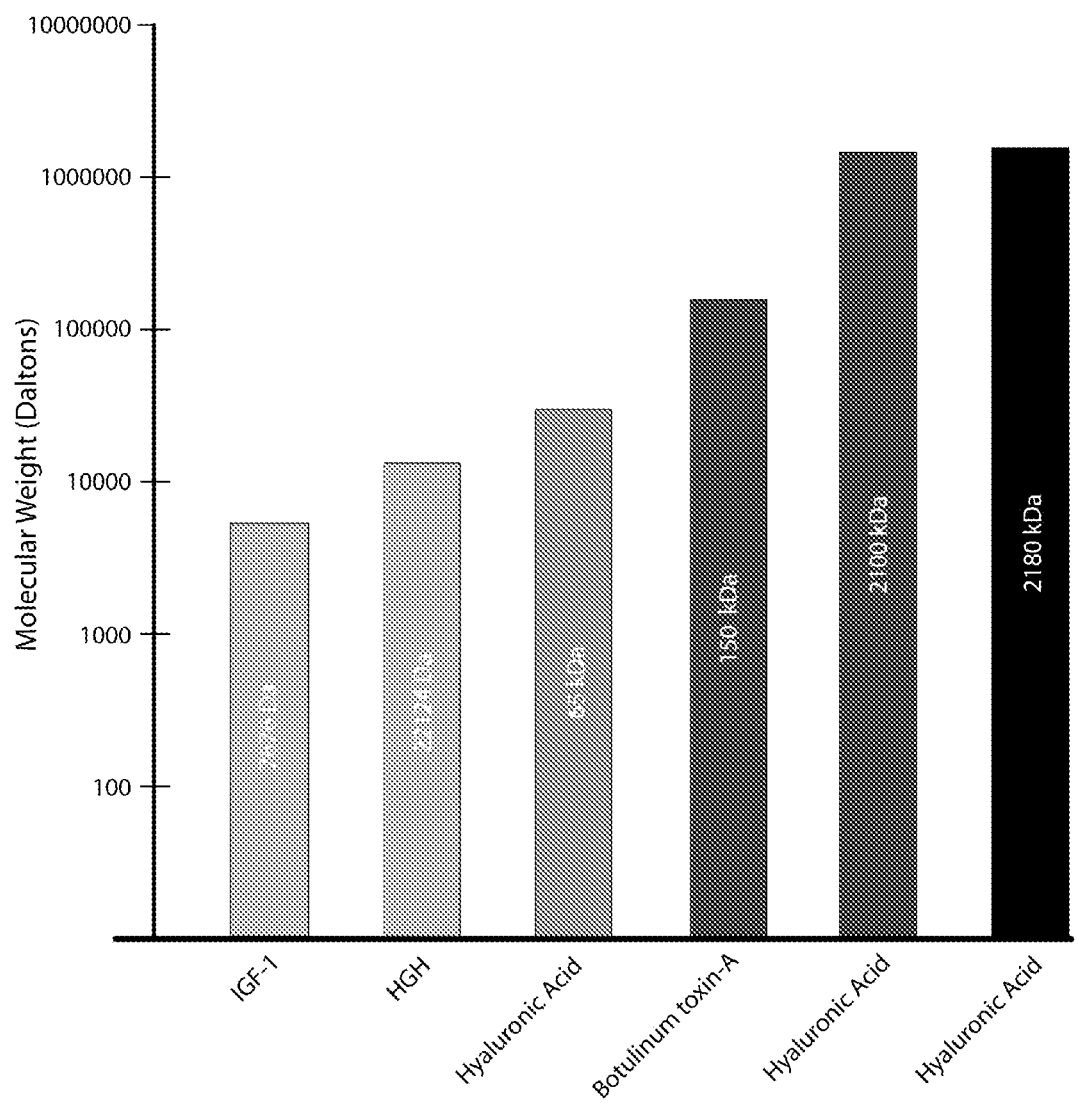
FIG. 6 shows molecular weight range of compounds delivered into and through human skin using the photokinetic system. Significant quantities were delivered when compared to passive permeation control conditions. The photokinetic intradermal and transdermal delivery system provided surprising and unexpected results as the molecules tested herein are well beyond (>4000 times) the 500 Dalton upper molecular weight useful limit normally associated with permeation into and through intact (non-porated) skin.

Now turning to FIG. 5. For drugs to permeate through skin as in transdermal drug delivery, they must first be transported into the skin and provide an intradermal presence before diffusing out of the skin into deeper tissue regions. The intradermal drug concentration is of particular importance for applications requiring the biological active substance to reside within the skin to provide a biological affect on the skin itself. Photokinetic intradermal/transdermal delivery is an active delivery technology wherein a biologically active substance permeates into and/or through skin at a higher flux rate than what could be achieved with passive diffusion alone. Furthermore, the delivery of the biologically active substance can be controlled or modulated in order to allow the concentration of the biologically active substance to be regulated, and to preferentially accumulate intradermally (preferably not penetrating any further) within the skin and have an effect primarily on the skin itself. FIG. 5 represents the exemplary method to determine drug concentration within the skin.

Passive and photokinetic permeation conditions are similar except for the photokinetic donor chamber is provided with pulsed incoherent light as pervious described. The method of determining intradermal concentration of the drug may comprise the following steps: the donor drug formulation 24 is removed from the donor chamber by several washes of the donor chamber 21 with demonized water. Skin is separated from both Franz apparatus chambers 21 and 22.

The area of the skin held between the two chambers is cut away from the skin that was positioned under the flanges of the donor and recipient chambers providing a section of skin that was exposed to the experimental conditions. The excised skin sample is then frozen in liquid nitrogen. The frozen skin sample is then placed in a cryogenic tissue pulverizer (Fisher Scientific) pre-cooled in liquid nitrogen and freeze fractured. The pulverized freeze fractured tissue is weighed and placed into an extraction buffer appropriate for the selected drug analysis. The tissues are toughly mixed with the buffer solution and centrifuged to separate the solid tissue components from the extraction buffer. Supernates from the centrifuged samples are analyzed for subject drug concentration and protein concentration. Protein concentration determination is used to normalize the drug extraction efficiency between the samples.

Procurement of Human Skin for in vitro Testing

Human split thickness skin harvested from cadaver donors (skin removed with a dermatome including the entire epidermis and part of the dermis) was obtained from Allosource International (Centennial, Colo.). Spit thickness skin had a thickness of approximately 0.625 mm to 2.0 mm thick. Procured skin was placed immediately in pre-cooled RPMI 1640 medium with antibiotics/antimycotics and refrigerated at 4° C. until used. Skin was used within 96 hours after procurement.

4. Patch for Dermal Treatment

In certain embodiments, the methods of the invention utilize a dermal patch to facilitate the delivery of a biologically active substance/molecule. In certain embodiments, the patch may take the form of a mask for topical use (e.g., face mask). In certain embodiments, the patch allows the controlled release of active ingredients therein (e.g., the biologically active substance/molecule). The dermal patch may in some instance overcome the hydrophobic resistance typical of the skin.

In certain embodiments, the subject dermal patch is biodegradable, and may be of vegetal origin.

In certain embodiments, the subject dermal patch is a pre-shaped dermal treatment patch or mask that does not contain substances like Tissue Non-Tissue (TNT), or polymers such as polyester or polyacrylate, in which the desired active ingredients can be inserted.

In certain embodiments, the subject dermal patch or mask does not require an adhesive layer in order to be applied to the skin.

In certain embodiments, the subject dermal mask or patch is free of preservatives and/or perfumes.

In certain embodiments, the subject dermal patch or mask contains a polysaccharide-based vegetal matrix, which may be extracted from red algae (e.g., *Chondrus crispus*), and which may be rich in polymeric thickeners.

In certain embodiments, the subject patch or mask are for use in cosmetic and/or pharmaceutical/therapeutic applications.

In certain embodiments, the base of the subject patch or mask is a matrix of 100% plant origin, such as one obtained from an extract of red algae (e.g., *Chondrus crispus*), which may contain polysaccharides with thickening properties, and which may have the peculiarity to form a biological network. Such polysaccharides are used in food and cosmetic products for their structuring properties, e.g. for enhancing viscosity and/or stability.

The polysaccharides of *Chondrus crispus* may generate a network that imparts a three-dimensional structure to the dermal patch or mask. This structure is similar to that obtained, e.g., by using silicones, and may confer similar structural properties such as transparency, elasticity, and flexibility optimal to be easily applied to the skin; resistance, adhesive strength, possibility to be removed and replaced while maintaining the same shape, etc. After use, the patch can be easily removed from the skin without leaving residues.

The patch or mask of this invention is a highly viscose fluid, structured in the form of a gel, which is resistant and can be safely applied to the human skin. The patch forms a film on the skin, allowing hydration by water release from its vegetal matrix as well as gradual and controlled release of any cosmetic, dermatological, or pharmaceutical active ingredient incorporated in the formulation.

These features are maintained as long as the water content of this structure remains unchanged: as the water evaporates, the structure tends to dry up and lose the above characteristics. However, the process of drying is much slower than with other cosmetic treatments of skin, usually from 10 to 30 min., occurring only several hours after air exposure.

Importantly, unlike the commonly used patches, which contain a synthetic polymeric support to guarantee the structure and mechanical characteristics of the patch, the matrix of the patch subject of this invention may be totally natural and thus biodegradable.

At lower concentrations of red algae (e.g., *Chondrus crispus*) extract, the required structural characteristics might not be obtained: the product forms a classical viscous gel, but remains liquid, and does not maintain the shape when subjected to mechanical stress, such as the removal from the blister or when applied on the skin.

Conversely, at higher concentrations of red algae extract, the mixture becomes clearer and fails to gel.

At specific concentrations, it is possible to obtain a gel structure with such interesting mechanical performance.

The stability of the dermal patch in its original sealed blister has been tested at 1, 3, and 12 months, by visual inspection and tests of adhesion to the skin, and no significant loss of property was observed.

The patch compositions of the invention can be prepared by conveniently mixing the components of the mixture at suitable temperatures.

The blend of ingredients at the selected temperature is a viscose fluid that can be mixed with normal equipment, such as classical mixers.

The mixture may be kept at constant temperature, from 30 to 90° C., e.g., closer to the upper limit of 90° C., under constant stirring at 1 to 30 rpm, e.g., around 10 rpm.

When cooled down gradually to room temperature, the obtained product is a highly resistant, transparent solid, showing high elasticity and adhesion to the skin. The appearance, texture and resistance of the finished product is comparable to those of similar silicone-based products, but with the advantage of being natural.

As already mentioned above, the product maintains these structural characteristics until the level of hydration is constant.

The product may contain any cosmetic or dermopharmaceutical active ingredient, incorporated in the solution or dispersed in the water entrapped by the network of polysaccharides.

The moulding may take place in a container—a "blister"—of the desired shape. As the liquid cools, the product takes the shape in the blister.

Accordingly, single patches of various size and shape can be prepared, suited to be used for different applications.

The exact amount of product can be dosaged through a timed and heated electronic valve under controlled temperature, specifically designed and adapted for this process. The correct opening time of the valve may determine the flow of the product and the right dosage. The blister containing the product is then sealed, e.g., by an aluminium/polyethylene tie layer. Then the blister is die-cut to obtain the desired shape.

The sealed containers allow the patch to retain the structural and mechanical properties until the moment of application.

In one embodiment of the invention, the initial mixture of ingredients is prepared by dispersing *Chondrus crispus* (SETALG) in a blend of glycol, glycerin, or other moisturising substances until a homogeneous dispersion is obtained without any lumps.

In another embodiment, during the initial mixing phase, 75% of the water needed for the production of the batch is heated to 90° C. After reaching this temperature, the suspension is added under vigorous stirring, and then it is left to cool to 50-60° C. In this embodiment, the water soluble active ingredient is dispersed in the remaining water, and then it is added to the hot phase under stirring to obtain a complete dispersion.

In a yet further embodiment, casting takes place preferably at a temperature between 50 and 60° C., and the dosage is performed through a nozzle connected to a valve attached to the interior of the mixer. The pneumatically controlled valve opens for the time necessary to let through the desired quantity of product, the opening time of the valve is adjusted by a pneumatic timer and the dosage is done in the same blister in which the product cools down, determining the product shape.

The entire process can be done in a sterile environment, using sterile materials, e.g., for the preparation of patches without preservatives, since the ingredients used in the mixture may provide a substrate for the proliferation of microorganisms (similar polysaccharides are used in the culture broths to incubate microorganisms in laboratory tests).

The process can also be carried out in an inert atmosphere of nitrogen, in order to limit any possible oxidative processes on the product.

The products obtained as described above can be used in both cosmetics and therapeutic applications.

For cosmetic/therapeutic uses, the products of the invention are appropriately formulated, possibly with other dermatologically active substances.

Formulations appropriate to the purpose of this invention include all types of cosmetic and dermopharmaceutical ingredients, such as the molecules described herein.

In addition to the ingredients used to formulate the products of this invention, the formulation may also contain other biologically active ingredients and excipients, such as surfactants, emollients, emulsifiers, solvents, moisturizers, enhancers of percutaneous absorption, and in general all types of ingredients, well-known to the formulators of cosmetic and pharmaceutical products.

EXAMPLES

All examples in U.S. Pat. No. 7,458,982, U.S. Pat. No. 7,854,753, European patent EP1556061B2, and PCT publication WO 2009-124763 A2, including all associated data and figures referenced therein, are hereby incorporate herein by reference.

Part of the Examples in WO 2009-124763 A2 are reproduced below as Example 1.

Example 1

Base formulation 1

| Ingredients | INCI Name | % |
|---|---|---|
| Water | Aqua | up to 100 |
| Methylpropanediol | Methylpropanediol | 10 |
| Glycerin | Glycerin | 20 |
| *Chondrus crispus* | *Chondrus crispus* | 2 |
| Active ingredient | INCI name of active ingredient | proper quantity |
| Preservative (if desired) | Preservative systems | proper quantity |

Base formulation 2

| Ingredients | INCI Name | % |
|---|---|---|
| Water | Aqua | up to 100 |
| Butylene glycol | Butylene glycol | 10 |
| Sorbitol solution 70% | Sorbitol, Aqua | 20 |
| *Chondrus crispus* | *Chondrus crispus* | 2 |
| Active ingredient | INCI name of active ingredient | proper quantity |
| Preservative (if desired) | Preservative systems | proper quantity |

Examples of use of patches as carriers for active ingredients are provided below.

Different patches have been prepared incorporating active ingredients for cosmetic use. In an exemplary embodiment, the method of preparation includes the following steps:

1. Mix all components, adding the components in the order shown above, heating at a temperature above 70° C., preferably at 90° C., under stirring.

2. Cast the mixture in the blisters, keeping the temperature of the nozzles preferably at around 50-60° C.

3. Close/seal the blister and allow to cool down to room temperature.

More specifically, the production of the mask takes place in a planetary mixer, equipped with a jacketing for heating with temperature control (thermostat).

The preparation is conducted as follows: The product *Chondrus crispus* is pre-dispersed in the mixture of glycerin and methylpropanediol until it forms an homogeneous dispersion without lumps. In the meantime, 75% of the water needed for the production of the batch is heated to 90° C.

After reaching this temperature, the suspension is added to the water under vigorous stirring, then it is left to cool to 50-60° C.

The water soluble active ingredient is dispersed in the remainder of the water, and then added to the hot phase under stirring, to obtain a complete dispersion. Finally the casting of the product can be started.

The casting takes place preferably at the temperature of 50 and 60° C., using a dosage system.

The dosage is performed by a nozzle connected to a valve, attached to the interior of the mixer; the pneumatically controlled valve opens for the time necessary to let through the desired quantity of product. The opening time of the valve is adjusted by a pneumatic timer.

The dosage is done in the same blister which, with the cooling, imparts the shape to the product.

The product is then allowed to cool down, and an aluminium/polythene tie layer sheet is applied to seal the blister.

The blister is then die-cut, reaching the desired final shape of the finished product.

A second exemplary patch contains sodium hyaluronate, as described in table immediately below.

| Components | INCI Name | % |
|---|---|---|
| Water | Aqua | 67.5 |
| Methylpropanediol | Methylpropanediol | 10 |
| Glycerin | Glycerin | 20 |
| *Chondrus crispus* | *Chondrus crispus* | 2 |
| Sodium Hyaluronate (1800-2200 kDa) from Shandong Freda Biopharm | Sodium Hyaluronate | 0.5 |

The method of preparation is similar to that of the previous example immediately above. This patch has been shown to recover the correct hydration level and is useful to treat the most dry/dehydrated areas of the skin. The efficacy of this eye contour patch has been tested successfully in clinical studies on volunteers, where the hydrating and decongesting efficacy for this area has been evaluated.

These gel patches have been used alone, and it has been observed that there was a delivery of hydrosoluble active ingredients to the skin in a time-controlled manner on the human skin, by means of osmotic processes and occlusive effect. Therefore, the invention products fulfill the requirements for dermal masks, preferentially for face treatment.

There are several advantages associated with the present invention respect to the common patches used for cosmetic and dermopharmaceutical applications, for example:
- the matrix is completely vegetal and biodegradable;
- the products show optimal structural features: elasticity, flexibility, resistance, adhesiveness, possibility to be removed and re-applied keeping the original shape, transparency;
- there is no need for pre-formed substrates like Tissue Non-Tissue (TNT) or polymers such as polyester or polyacrylate, in which the desired active ingredients are inserted and which require also an adhesive layer for adhesion to the skin;
- the patch itself has hydrating properties, thanks to its vegetable matrix structure;
- it is possible to produce masks without preservatives and/or perfumes;
- patches of any shape or size are easily obtained by casting the melted mixture into a proper mould (blister);
- the mask as such has an hydrating and lenitive effect to the skin;
- the masks are dermatologically safe.

Example 2

IGF-1 In Vitro Testing

Insulin like growth factor I (IGF-1) is a 70 amino acid polypeptide with 49% structural homology to insulin. The intradermal deposition of IGF-1, (MW=7,676 Da) at a donor concentration of 1.2 µg/ml in propylene glycol. Intradermal drug deposition for passive controls and photokinetic conditions was determined at 15, 30, and 60 minutes.

Insulin like growth factor 1 (IGF-1) was analyzed using commercially available ELISA kits according to manufacturer's instructions (Kit # Diagnostic System Laboratories, Webster, Tex.). Briefly, samples were incubated in 96-well plates coated with specific primary antibody for periods of time, washed, incubated with enzyme conjugate, washed again and then secondary HRP conjugated antibodies were added. Color was developed using tetramethylbenzidine substrate and the reaction was stopped by adding sulfuric acid (0.2%). The plates were read on a microplate reader (ELX800, BioTek Instruments, Winooski, Vt.) at 450 nm. Standard curves were built for each analyte and the concentration in each sample was calculated from standard curve.

Figure 7:
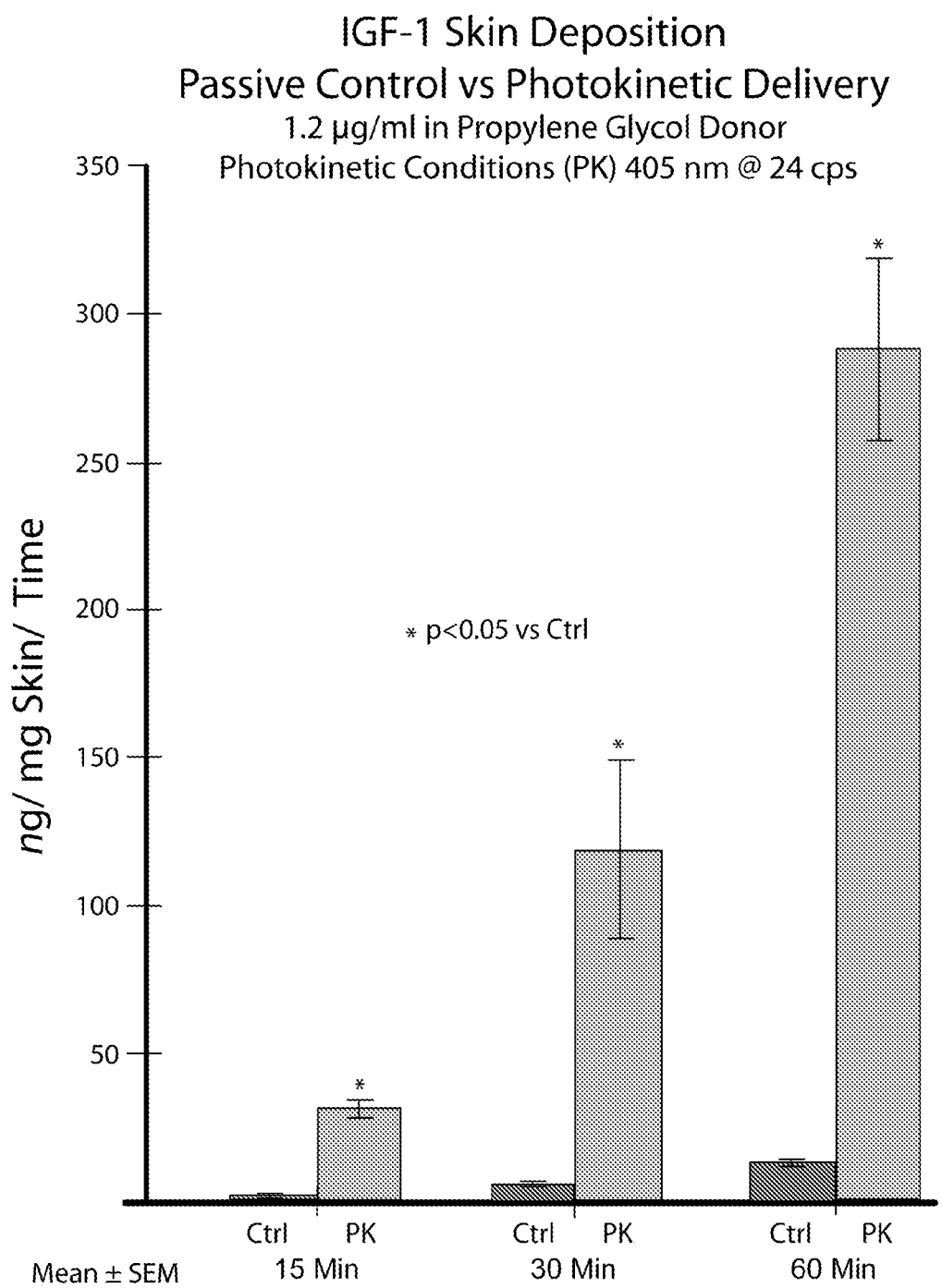
FIG. 7 shows that IGF-1 was delivered into intact human skin at significantly higher concentrations compared to passive permeation, as measured at 15, 30 and 60 minutes.

FIG. 7 shows that IGF-1 was delivered into intact human skin at significantly higher concentrations compared to passive permeation, as measured at 15, 30 and 60 minutes. The data demonstrates that the photokinetic system facilitates and increases achievable tissue concentration of IGF-1 compared to passive permeation.

Example 3

Human Growth Hormone In Vitro Testing

Human growth hormone (HGH) with a molecular weight of 22,124 Da at a final donor concentration of 270 ng/ml was prepared in a formulation of 5% ethyl lactate, 30% propylene glycol, 1% hyaluronic acid, 0.1% laurocapram, 0.1% Neolone™ 850, with the balance as deionized water. Transdermal permeation under photokinetic conditions of 350 nm, 390 nm, 405 nm, and 450 nm at 24 CPS were evaluated at 24 hours and compared with passive permeation control samples.

Analytical assays performed by ELISA (Diagnostic System Laboratories, Webster, Tex.) were analyzed using commercially available kits according to manufacturer's instructions. Briefly, samples were incubated in 96-well plates coated with specific primary antibody for periods of time, washed, incubated with enzyme conjugate, washed again and then secondary HRP conjugated antibodies were added. Color was developed using tetramethylbenzidine substrate, and the reaction was stopped by adding sulfuric acid (0.2%). The plates were read on a microplate reader (ELX800, BioTek Instruments, Winooski, Vt.) at 450 nm. Standard curves were built for each analyte and the concentration in each sample was calculated from standard curve.

Figure 8:
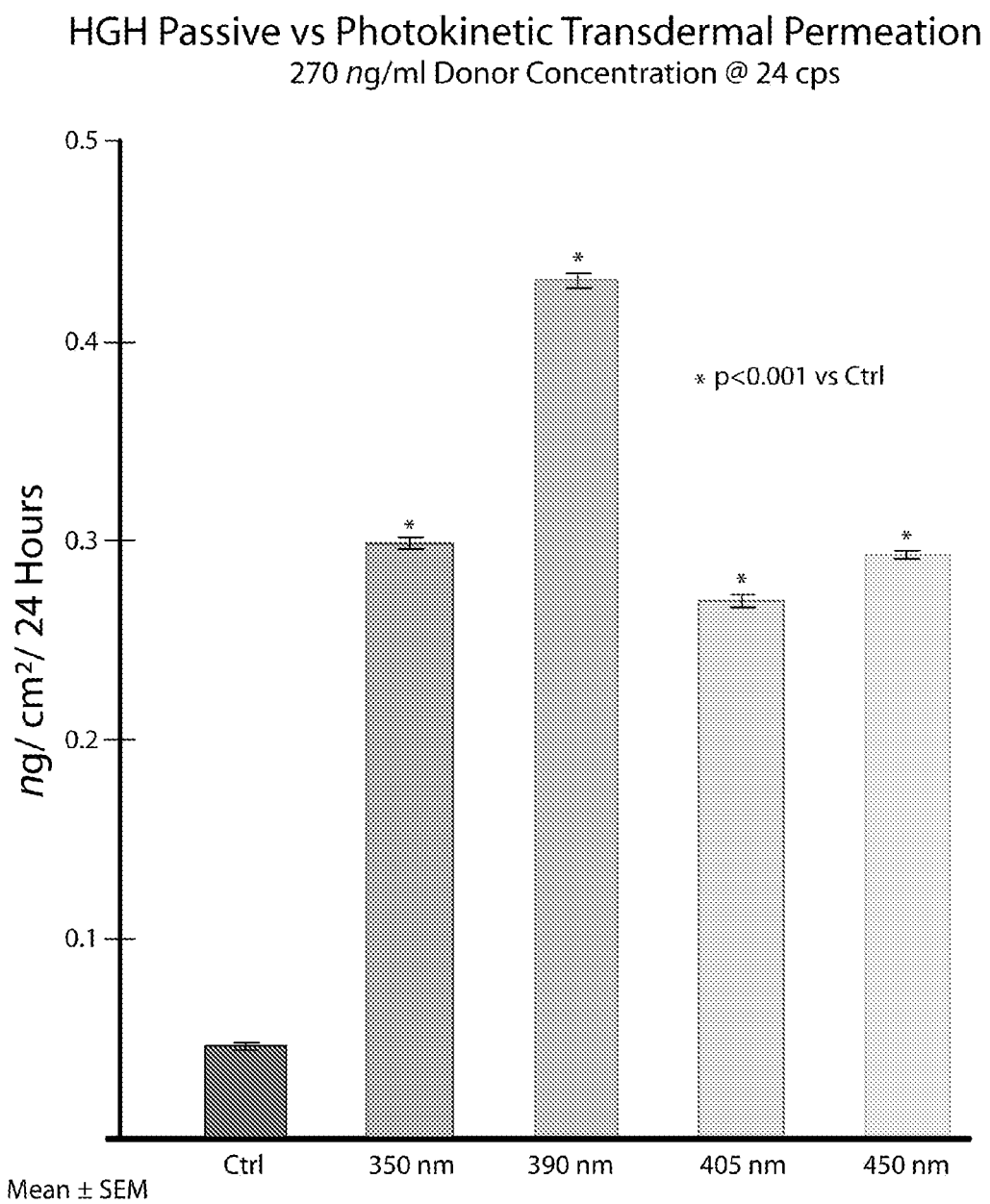
FIG. 8 shows human growth hormone (HGH) transdermal permeation quantities as measured at 24 hours exposed to 4 wavelengths of light pulsed at 24 cycles per second (24 cps).

FIG. 8 shows human growth hormone (HGH) transdermal permeation quantities as measured at 24 hours exposed to 4 wavelengths of light pulsed at 24 cycles per second (24 cps). The data demonstrates that the photokinetic system provides a significantly increased achievable transdermal permeation fluxes of HGH compared to passive permeation ($p<0.001$).

Example 4

Hyaluronic Acid In Vitro Testing

Hyaluronic acid (or hyaluronate) is an anionic, nonsulfated glycosaminoglycan, and is available in various molecular weights. Hyaluronic acid with a molecular weight 69,000 Daltons (69 kDa) at a final donor concentration of 2% w/w, in a formulation of 5% ethyl lactate, 30% propylene glycol, 1% hyaluronic acid, 0.1% laurocapram, 0.1% Neolone™ 850, and with the balance as deionized water, was assessed under various photokinetic conditions for transdermal fluxes and intradermal deposition.

Analytical assays performed by ELISA (Diagnostic System Laboratories, Webster, Tex.) were analyzed using commercially available kits according to manufacturer's instructions. Briefly, samples were incubated in 96-well plates coated with specific primary antibody for periods of time, washed, incubated with enzyme conjugate, washed again and then secondary HRP conjugated antibodies were added. Color was developed using tetramethylbenzidine substrate and the reaction was stopped by adding sulfuric acid (0.2%). The plates were read on a microplate reader (ELX800, BioTek Instruments, Winooski, Vt.) at 450 nm. Standard curves were built for each analyte and the concentration in each sample was calculated from standard curve.

Figure 9A:
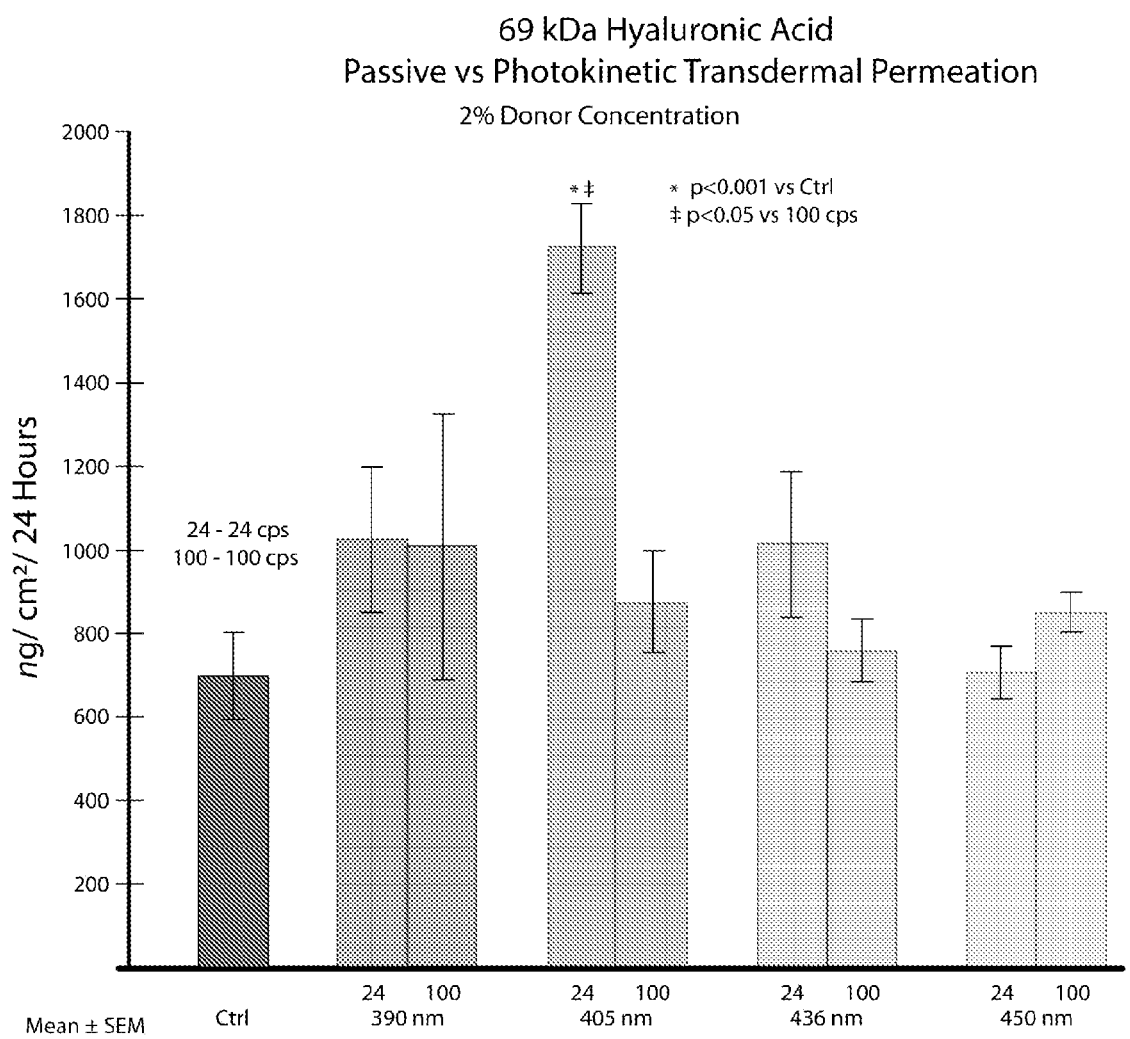
FIG. 9A shows transdermal permeation of 69 kDa hyaluronic acid, determined under photokinetic conditions of 390 nm, 405 nm, 436 nm, and 450 nm light pulsed at 24 cycles per second (cps) and 100 cps compared to passive permeation at 24 hours.

FIG. 9A show transdermal permeation of 69 kDa hyaluronic acid, determined under photokinetic conditions of 390 nm, 405 nm, 436 nm, and 450 nm light pulsed at 24 cycles per second (cps) and 100 cps compared to passive permeation at 24 hours. As shown for this particular molecule, photokinetic transdermal flux rates using 405 nm light pulsed at 24 cps were significantly higher than passive permeation ($p<0.001$). The flux rate achieved using 405 nm light pulsed at 24 cps was significantly higher than 405 nm light pulsed at 100 cps ($p<0.05$).

Figure 9B:
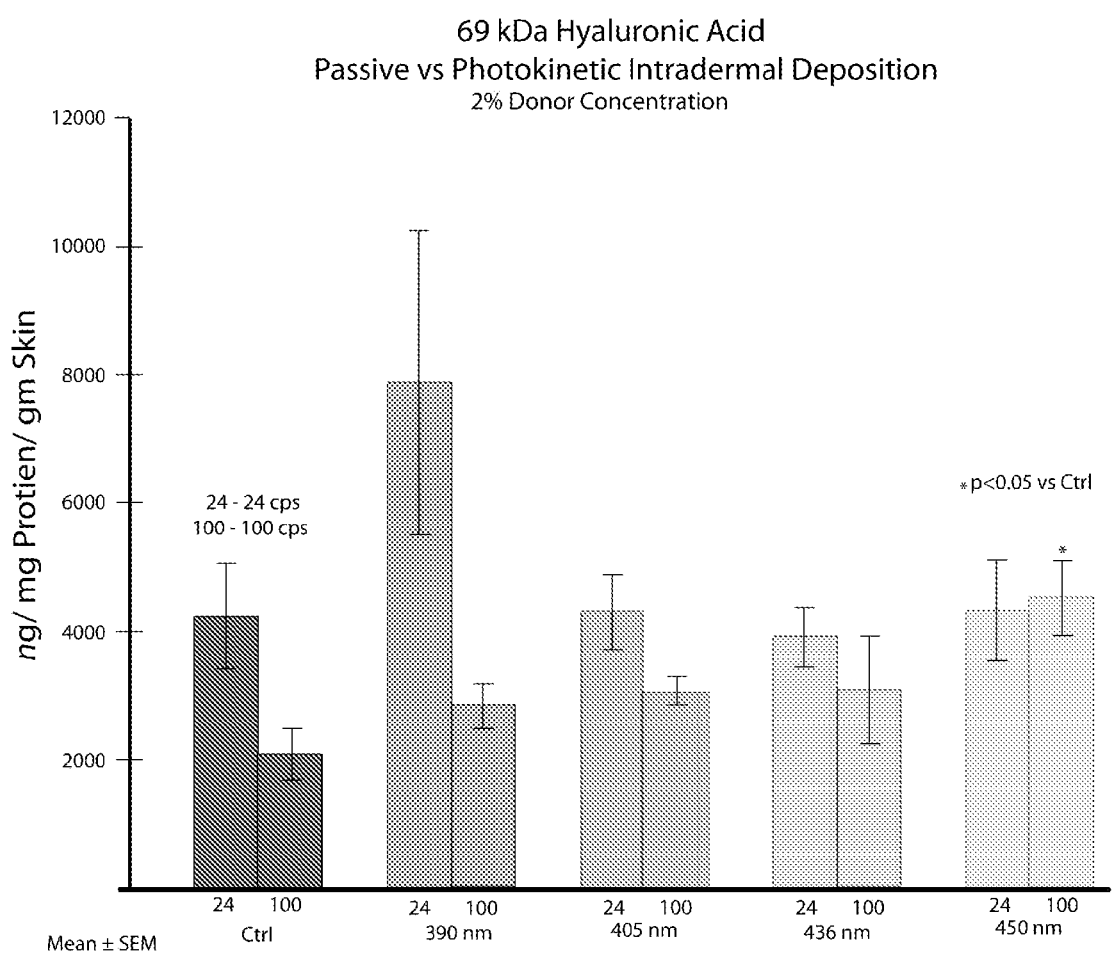
FIG. 9B shows intradermal deposition of 69 kDa hyaluronic acid, determined under photokinetic conditions of 390 nm, 405 nm, 436 nm, and 450 nm light pulsed at 24 cycles per second (cps) and 100 cps compared to passive deposition at 24 hours.

FIG. 9B shows intradermal deposition of 69 kDa hyaluronic acid, determined under photokinetic conditions of 390 nm, 405 nm, 436 nm, and 450 nm light pulsed at 24 cycles per second (cps) and 100 cps compared to passive deposition at 24 hours. Separate controls were established for both the 24 cps and 100 cps groups. As shown, for this particular molecule, the photokinetic condition of 450 nm light pulsed at 100 cps produced significantly higher intradermal deposition compared to the passive control ($p<0.05$).

Example 5

Botulinum Toxin Type A In Vitro Testing

Botulinum toxin type A with a molecular weight of about 150 kDa (Botox® Allergan Irvine, Calif.) was dissolved in a formulation comprising 5% ethyl lactate, 30% propylene glycol, 1% hyaluronic acid, 0.1% Neolone™ 850 with the balance as deionized water providing at a finale concentration of 2 units botulinum type A per mL. The botulinum formulation was used in the photokinetic testing apparatus previously described and evaluated at 405 nm and 450 nm for 24 and 100 cycles per second over 24 hours for both transdermal and intradermal drug concentration.

Samples were analyzed with a fluorescent reporter assay (Biosentinnel Pharmaceuticals, Madison Wis.) according to manufacturer's instructions. Briefly, recipient chamber and tissue extraction samples were incubated in 96-well plates with specific primary antibody conjugated with a fluorescent enzyme for periods of time, washed, incubated with substrate and the fluorescent intensity was measured. Standard curves were built for each analyte and the concentration in each sample was calculated from standard curve. Transdermal fluxes are expressed as nanograms (ng)/cm$^2$ of exposed skin/at 24 hours. Tissue deposition analysis incorporated a measurement of the protein content in the extracted samples as a method to normalize the extraction efficiency and are expressed as units of botulinum toxin type A/mg protein/mg skin.

Transdermal results for control passive permeation and 24 hour photokinetic exposure at 405 nm and 450 nm pulsed at 24 and 100 CPS are presented in FIG. 10A and FIG. 10B.

Example 6

Transdermal/Intradermal Delivery of 2,100 kDa Hyaluronic Acid

Hyaluronic acid (or hyaluronate) is an anionic, nonsulfated glycosaminoglycan and is available in various molecular weights. Hyaluronic acid with a molecular weight of 2,100,000 Daltons (2,100 kDa) at a final donor concentration of 1% w/w in a formulation of 5% ethyl lactate, 30% propylene glycol, 1% hyaluronic acid, 0.1% laurocapram, 0.1% Neolone™ 850, and with the balance as deionized water, was assessed under various photokinetic conditions for transdermal fluxes and intradermal deposition.

Analytical assays performed by ELISA were analyzed using commercially available kits according to manufacturer's instructions. Briefly, samples were incubated in 96-well plates coated with specific primary antibody for periods of time, washed, incubated with enzyme conjugate, washed again and then secondary HRP conjugated antibodies were added. Color was developed using tetramethylbenzidine substrate and the reaction was stopped by adding sulfuric acid (0.2%). The plates were read on a microplate reader (ELX800, BioTek Instruments, Winooski, Vt.) at 450 nm. Standard curves were built for each analyte and the concentration in each sample was calculated from standard curve.

Transdermal fluxes are expressed as nanograms (ng)/cm$^2$ of exposed skin/at 24 hours.

Tissue deposition analysis incorporated a measurement of the protein content in the extracted samples as a method to normalize the extraction efficiency and are expressed as units of hyaluronic acid/mg protein/mg skin.

Figure 11A:
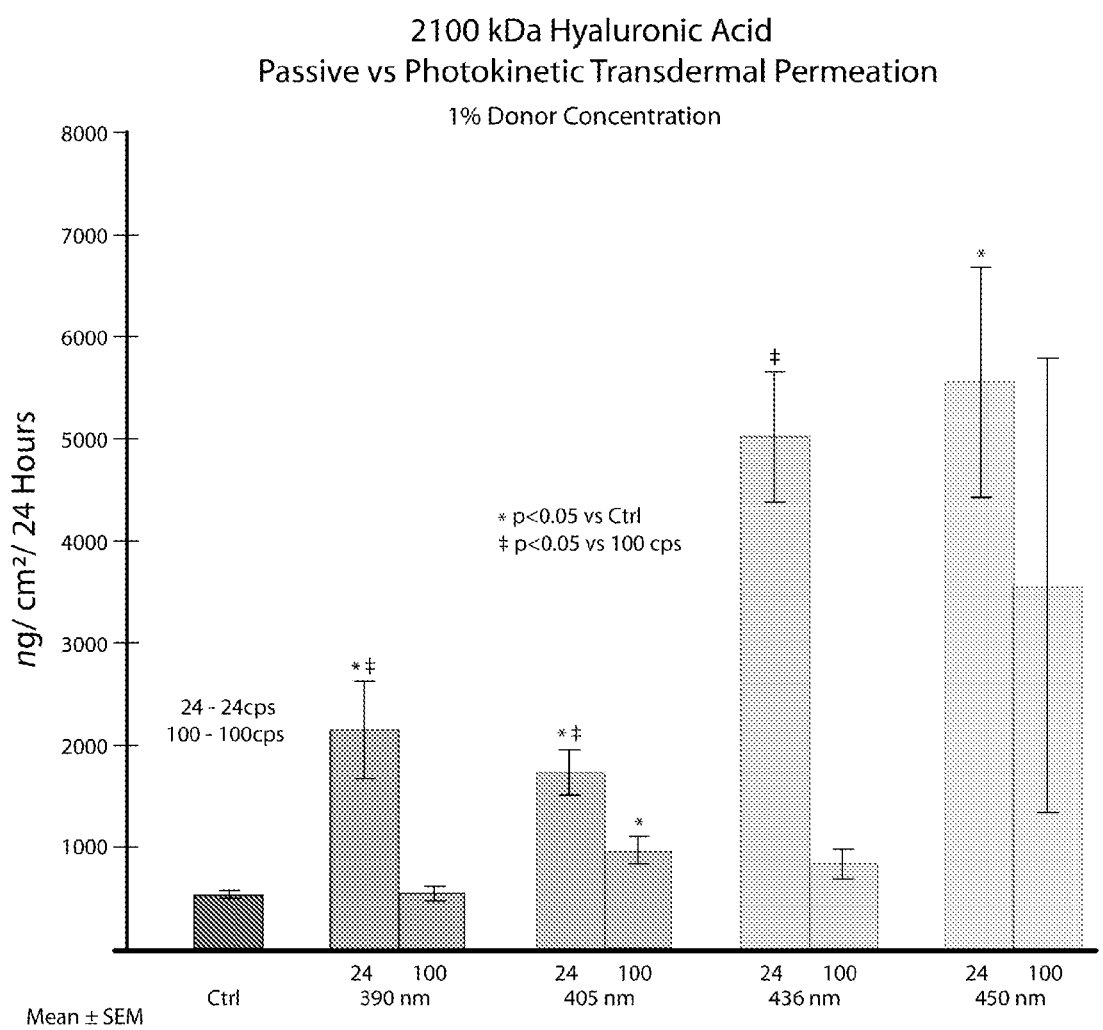
FIG. 11A shows transdermal permeation of 2,100 kDa hyaluronic acid determined under photokinetic conditions of 390 nm, 405 nm, 436 nm, and 450 nm light pulsed at 24 cycles per second (cps) and 100 cps compared to passive permeation at 24 hours.

FIG. 11A shows transdermal permeation of 2,100 kDa hyaluronic acid determined under photokinetic conditions of 390 nm, 405 nm, 436 nm, and 450 nm light pulsed at 24 cycles per second (cps) and 100 cps compared to passive permeation at 24 hours. As shown for this particular molecule, photokinetic transdermal flux rates using 390 nm, 405 nm, and 450 nm light pulsed at 24 cps, and 405 nm light pulsed at 100 cps were significantly higher than passive permeation control samples ($p<0.05$). The flux rate achieved using 390 nm, 405 nm, and 436 nm light pulsed at 24 cps was significantly higher than 390 nm, 405 nm, and 436 nm light pulsed at 100 cps ($p<0.05$).

Figure 11B:
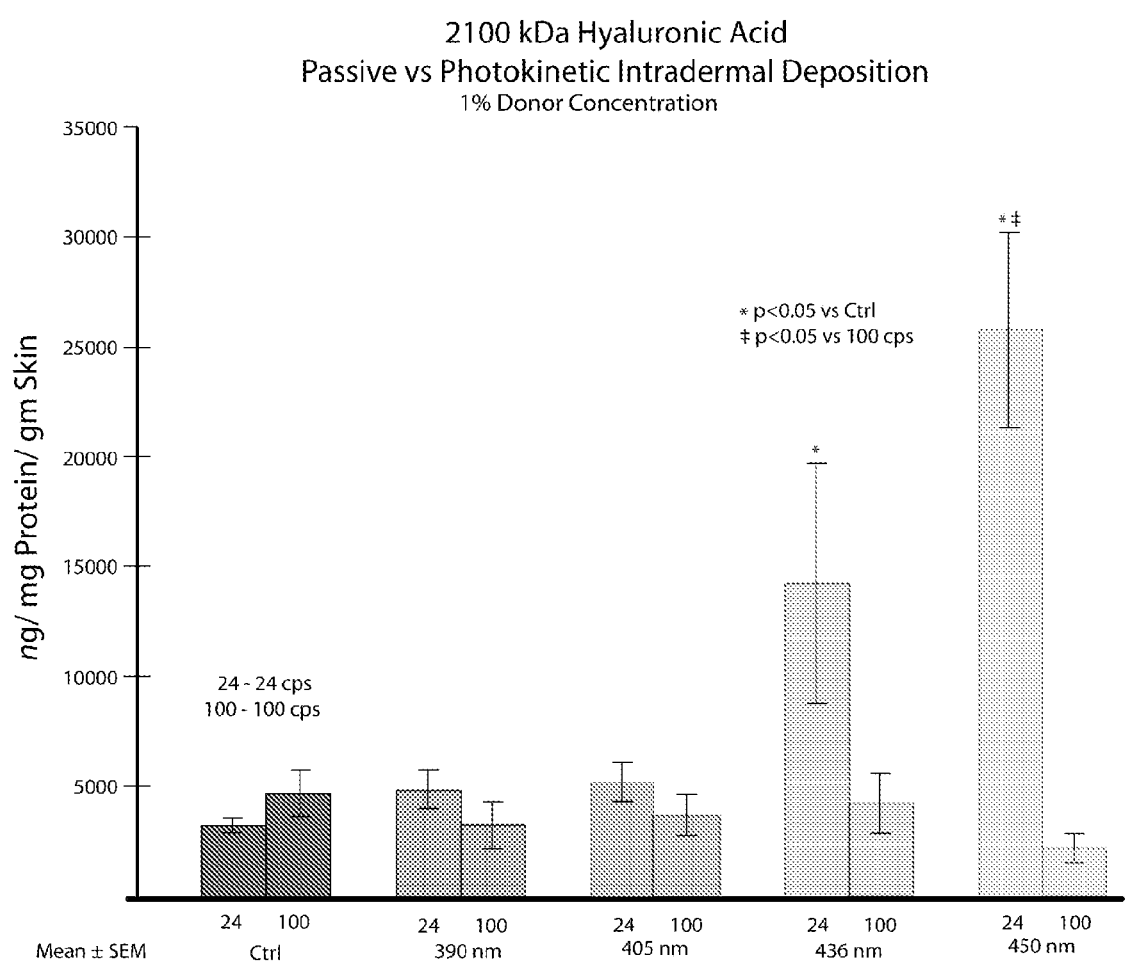
FIG. 11B shows intradermal deposition of 2,100 kDa hyaluronic acid determined under photokinetic conditions of 390 nm, 405 nm, 436 nm, and 450 nm light pulsed at 24 cycles per second (cps) and 100 cps compared to passive deposition at 24 hours.

FIG. 11B shows intradermal deposition of 2,100 kDa hyaluronic acid determined under photokinetic conditions of 390 nm, 405 nm, 436 nm, and 450 nm light pulsed at 24 cycles per second (cps) and 100 cps compared to passive deposition at 24 hours. Separate controls were established for both the 24 cps and 100 cps groups. As shown, for this particular molecule, the photokinetic conditions of 436 nm and 450 nm light pulsed at 24 cps produced significantly higher intradermal deposition compared to the passive controls ($p<0.05$). 450 nm light pulsed at 24 cps demonstrated significantly higher skin deposition than any of the light groups pulsed at 100 cps ($p<0.05$).

Example 7

Intradermal Delivery of Hyaluronic Acid 2,180,000 Daltons (2,180 kDa) at 15, 30 and 60 Minute Passive Control Vs. Photokinetic Exposure of 3 Formulations This example demonstrates the unexpectedly efficient intradermal delivery of a biologically active substance (HA) using a combination of the photokinetic method and the subject dermal patch containing a red algae polysaccharide-based matrix (e.g., an extract of Chondrus crispus at 2% by weight of the dermal patch).

Gel Formulation

1% hyaluronic acid, 63.9% citrus nobilis (fruit) extract, 35% propylene glycol with 0.1% preservative Emulsion Cream Base 1% hyaluronic acid in 87.9% Citrus nobilis (fruit) extract, 4% Olea Europaea Olive Fruit Oil, Hydrogenated Olive Oil, 2.5% Sucrose Palmitate, 2% Squalene, 1% Cetearyl Alcohol, 0.5% Sucrose Triesterate with 0.1% preservatives.

Patch Preparation as Per Example 1

0.5% hyaluronic acid in a patch, as described above.

Analytical assays performed by ELISA were analyzed using commercially available kits according to manufacturer's instructions. Briefly, samples were incubated in 96-well plates coated with specific primary antibody for periods of time, washed, incubated with enzyme conjugate, washed again and then secondary HRP conjugated antibodies were added. Color was developed using tetramethylbenzidine substrate and the reaction was stopped by adding sulfuric acid (0.2%). The plates were read on a microplate reader (ELX800, BioTek Instruments, Winooski, Vt.) at 450 nm. Standard curves were built for each analyte and the concentration in each sample was calculated from standard curve.

Tissue deposition analysis incorporated a measurement of the protein content in the extracted samples as a method to normalize the extraction efficiency and are expressed as units of hyaluronic acid/mg protein/mg skin at the 3 time points of 15, 30 and 60 minutes.

Figure 12:
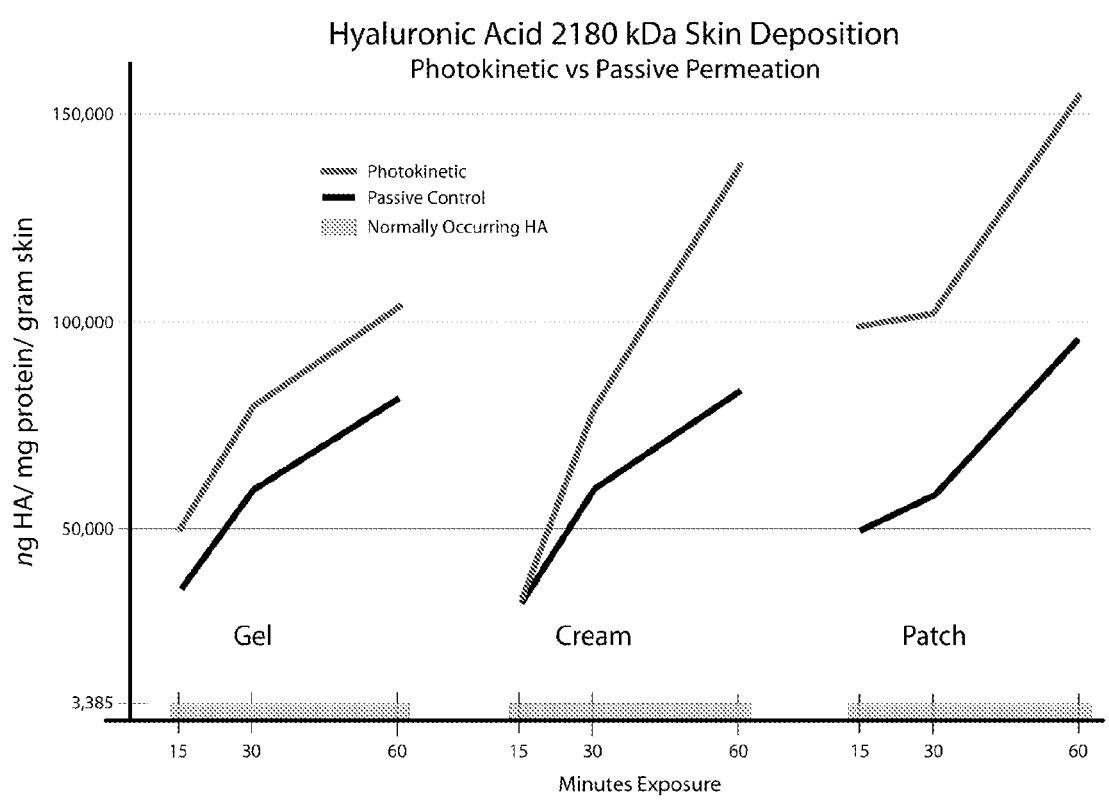
FIG. 12 shows intradermal deposition of hyaluronic acid formulated in a gel (1% HA), a cream (1% HA) and patch (0.5% HA) at 15, 30 and 60 minutes.

FIG. 12 shows intradermal deposition of 2,180 kDa hyaluronic acid formulated in a gel (1% HA), a cream (1% HA), and a patch (at about half the concentration of 0.5%), under photokinetic conditions of 450 nm light pulsed at 100 cps at 15, 30, and 60 minutes of exposure compared to passive deposition controls taken at the same time points. As shown, the passive deposition of the gel and emulsion cream formulations produced neatly identical deposition concentrations, while the patch formulation offered an increased intradermal at the 15 and 60 minute time points. Under photokinetic conditions of 450 nm light pulsed at 100 cps, all 3 formulations had increased depositions concentration compared to passive controls at each time point. Surprisingly under photokinetic conditions, the patch formulation produced higher intradermal deposition compared to the gel or emulsion cream formulations.

Hyaluronic acid normally occurs within skin. Samples of skin not exposed to the topical hyaluronic acid formulations demonstrated a level of 3,385 nanograms/milligram of skin. The three formulations produced increased skin deposition compared to normally occurring hyaluronic acid within the skin.

It is apparent, based on FIG. 12, that patch-mediated delivery of HA (at about half the concentration of 0.5%) is surprisingly more effective (about 200-300% more effective) compared to cream- or gel-mediated HA delivery, even though similar photokinetic parameters were used in the experiments.

Example 8

Hyaluronic Acid Patch on a 55 Year Old Male Forehead Wrinkle

One half of a prominent forehead wrinkle was covered with the patch and was exposed to 450 nm light at 100 CPS for one hour. After one hour the patch was removed and the two halves of the same wrinkle were evaluated. It was immediately obvious that the exposed forehead area had a pronounced reduction in wrinkle depth and prominence.

REFERENCES

Barrak Al-Qallaf, Diganta Bhusan Das, Daisuke Mori and Zhanfeng Cui, Modeling transdermal delivery of high molecular weight drugs from microneedle systems, *Phil. Trans. R. Soc. A* 365, 2951-2967, 2007.

Beatrice M. Magnusson, Yuri G. Anissimov, Sheree E. Cross, and Michael S. Roberts, Molecular Size as the Main Determinant of Solute Maximum Flux Across the Skin, *J Invest Dermatol* 122: 993-999, 2004.

Eseldin Kelebl, Rakesh Kumar Sharma, Esmaeil B mosa, Abd-alkadar Z aljahwi, Transdermal Drug Delivery System-Design and Evaluation *International Journal of Advances in Pharmaceutical Sciences* 1: 201-211, 2010.

Ritesh Kumar and Anil Philip, Modified Transdermal Technologies: Breaking the Barriers of Drug Permeation via the Skin, *Tropical Journal of Pharmaceutical Research*, 6(1): 633-644, 2007.

All references cited are incorporated herein by reference.

Annex VI (Part 1)
List of preservatives allowed

| Reference number a | Substance b | Maximum authorized concentration c | Limitations and requirements d | Conditions of use and warnings which must be printed on the label e |
|---|---|---|---|---|
| 1a | Salts of benzoic acid other than that listed under reference number 1 and esters of benzoic acid | 0.5% (acid) | | |
| 1 | Benzoic acid (CAS No 65-85-0) and its sodium salt (CAS No 532-32-1) | Rinse-off products, except oral care products: 2.5% (acid) Oral care products: 1.7% (acid) Leave-on products: 0.5% (acid) | | |
| 2 | Propionic acid and its salts | 2% (acid) | | |
| 3 | Salicylic acid and its salts (*) | 0.5% (acid) | Not to be used in preparations for children under three years of age, except for shampoos | Not to be used for children under three years of age (1) |
| 4 | Sorbic acid (hexa-2,4-dienoic acid) and its salts | 0.6% (acid) | | |

Annex VI (Part 1)
List of preservatives allowed

| Reference number a | Substance b | Maximum authorized concentration c | Limitations and requirements d | Conditions of use and warnings which must be printed on the label e |
|---|---|---|---|---|
| 5 | Formaldehyde and paraformaldehyde (*) | 0.2% (except for oral hygiene) 0.1% (for oral hygiene) concentrations expressed as free formaldehyde | Prohibited in aerosol dispensers, except for foams | |
| 7 | Biphenyl-2-ol (o-phenylphenol) and its salts | 0.2% expressed as the phenol | | |
| 8 | Zinc pyrithione (*) (CAS No 13463-41-7) | Hair products: 1.0% Other products: 0.5% | Rinse-off products only No use in products for oral hygiene | |
| 9 | Inorganic sulphites and hydrogensulphites (*) | 0.2% expressed as free SO2 | | |
| 11 | Chlorobutanol (INN) | 0.5% | Prohibited in aerosol dispensers (sprays) | Contains chlorobutanol |
| 12 | 4-hydroxybenzoic acid and its salts and esters | 0.4% (acid) for 1 ester 0.8% (acid) for mixtures of esters | | |
| 13 | 3-Acetyl-6-methylpyran-2,4(3H)-dione (Dehydroacetic acid) and its salts | 0.6% (acid) | Prohibited in aerosol dispensers (sprays) | |
| 14 | Formic acid and its sodium salt | 0.5% (expressed as acid) | | |
| 15 | 3,3'-Dibromo-4,4'-hexamethylenedioxydibenzamidine (Dibromohexamidine) and its salts (including isethionate) | 0.1% | | |
| 16 | Thiomersal (INN) | 0.007% (of Hg). If mixed with other mercurial authorized by this Directive, the maximum concentration of Hg remains fixed at 0.007% | For eye make-up and eye make-up remover only | Contains thiomersal |
| 17 | Phenylmercuric salts (including borate) | 0.007% (of Hg). If mixed with other mercurial compounds authorized by this Directive, the maximum concentration of Hg remains fixed at 0.007% | For eye make-up and eye make-up remover only | Contains phenylmercuric compounds |
| 18 | Undec-10-enoic acid and its salts | 0.2% (acid) | | |
| 19 | Hexetidine (INN) | 0.1% | Rinse-off products only | |
| 20 | 5-Bromo-5-nitro-1,3-dioxane | 0.1% | Rinse-off products only Avoid formation of nitrosamines | |
| 21 | Bronopol (INN) | 0.1% | Avoid formation of nitrosamines | |
| 22 | 2,4-Dichlorobenzyl alcohol | 0.15% | | |
| 23 | Triclocarban (INN) (*) | 0.2% | Purity criteria: 3,3',4,4'-Tetrachloroazobenzene <1 ppm; 3,3',4,4'-Tetrachloroazoxybenzene <1 ppm | |
| 24 | 4-Chloro-m-cresol | 0.2% | Prohibited in the products intended to come into contact with mucous membranes | |
| 25 | Triclosan (INN) | 0.3% | | |
| 26 | 4-Chloro-3,5-xylenol | 0.5% | | |
| 27 | 3,3'-Bis(1-hydroxymethyl-2,5-dioxoimidazolidin-4-yl)-1,1'-methylenediurea ("Imidazolidinyl urea") | 0.6% | | |
| 28 | Poly(1-hexamethylenebiguanide hydrochloride) | 0.3% | | |
| 29 | 2-Phenoxyethanol | 1.0% | | |
| 30 | Hexamethylenetetramine (methenamine) (INN) | 0.15% | | |
| 31 | Methenamine 3-chloroallylochloride (INNM) | 0.2% | | |
| 32 | 1-(4-Chlorophenoxy)-1-(imidazol-1-yl)-3,3-dimethylbutan-2-one | 0.5% | | |
| 33 | 1,3-Bis(hydroxymethyl)-5,5-dimethylimidazolidine-2,4-dione | 0.6% | | |
| 34 | Benzyl alcohol (*) | 1.0% | | |
| 35 | 1-Hydroxy-4-methyl-6-(2,4,4-trimethylpentyl)-2 pyridon and its monoethanolamine salt | 1% rinse-off products 0.5% other products | | |

Annex VI (Part 1)
List of preservatives allowed

| Reference number a | Substance b | Maximum authorized concentration c | Limitations and requirements d | Conditions of use and warnings which must be printed on the label e |
|---|---|---|---|---|
| 37 | 6,6-Dibromo-4,4-dichloro-2,2'-methylene-diphenol (Bromochlorophen) | 0.1% | | |
| 38 | 4-Isopropyl-m-cresol | 0.1% | | |
| 39 | Mixture of 5-Chloro-2-methyl-isothiazol-3(2H)-one and 2-Methylisothiazol-3(2H)-one with magnesium chloride and magnesium nitrate | 0.0015% (of a mixture in the ratio 3:1 of 5-Chloro-2-methyl-isothiazol-3(2H)-one and 2-Methylisothiazol-3(2H)-one | | |
| 40 | 2-Benzyl-4-chlorophenol (chlorophene) | 0.2% | | |
| 41 | 2-Chloroacetamide | 0.3% | | Contains chloroacetamide |
| 42 | Chlorhexidine (INN) and its digluconate, diacetate and dihydrochloride | 0.3% expressed as chlorhexidine | | |
| 43 | 1-Phenoxypropan-2-ol (*) | 1.0% | Only for rinse-off products | |
| 44 | Alkyl (C12-C22) trimethyl ammonium, bromide and chloride (*) | 0.1% | | |
| 45 | 4,4-Dimethyl-1,3-oxazolidine | 0.1% | The pH of the finished product must not be lower than 6 | |
| 46 | N-(Hydroxymethyl)-N-(dihydroxymethyl-1,3-dioxo-2,5-imidazolidinyl-4)-N'-(hydroxymethyl)urea | 0.5% | | |
| 47 | 1,6-Di(4-amidinophenoxy)-n-hexane (Hexamidine) and its salts (including isothionate and p-hydroxybenzoate) | 0.1% | | |
| 48 | Glutaraldehyde (Pentane-1,5-dial) | 0.1% | Prohibited in aerosols (sprays) | Contains glutaraldehyde (where glutaraldehyde concentration in the finished product exceeds 0.05%) |
| 49 | 5-Ethyl-3,7-dioxa-1-azabicyclo[3.3.0] octane | 0.3% | Prohibited in oral hygiene products and in products intended to come into contact with mucous membranes | |
| 50 | 3-(p-Chlorophenoxy)-propane-1,2-diol (chlorphenesin) | 0.3% | | |
| 51 | Sodium hydroxymethylamino acetate (Sodium hydroxymethylglycinate) | 0.5% | | |
| 52 | Silver chloride deposited on titanium dioxide | 0.004% calculated as AgCl | 20% AgCl (w/w) on TiO2 Prohibited in products for children under three years of age, in oral hygiene products and in products intended for application around the eyes and on the lips | |
| 53 | Benzethonium Chloride (INCI) | 0.1% | (a) Rinse-off products (b) Leave-on products other than for oral care use | |
| 54 | Benzalkonium chloride, bromide and saccharinate (*) | 0.1% calculated as benzalkonium chloride | | Avoid contact with eyes |
| 55 | Benzylhemiformal | 0.15% | Only for products to be removed by rinsing | |
| 56 | Iodopropynyl butylcarbamate; (IPBC); 3-Iodo-2-propynylbutylcarbamate CAS No: 55406-53-6 | (a) Rinse-off products: 0.02% (b) Leave-on products: 0.01%, except in deodorants/antiperspirants: 0.0075% | Not to be used in oral hygiene and lip care products. (a) Not to be used in preparations for children under three years of age except in bath products/shower gels and shampoos (b) Not to be used in body lotion and body cream (*) Not to be used in preparations for children under three years of age | (a) Not to be used for children under three years of age () (b) Not to be used for children under three years of age (*) |

Annex VI (Part 1)
List of preservatives allowed

| Reference number a | Substance b | Maximum authorized concentration c | Limitations and requirements d | Conditions of use and warnings which must be printed on the label e |
|---|---|---|---|---|
| 57 | Methylisothiazolinone (INCI) | 0.01% | | |
| 58 | Ethyl Lauroyl Arginate HCl (INCI) (*) (**)<br>Ethyl-N-alpha-dodecanoyl-L-arginate hydrochloride<br>CAS No 60372-77-2<br>EC No 434-630-6 | 0.4% | Not to be used in lip products, oral products and spray products | |

PREAMBLE
1. Preservatives are substances which may be added to cosmetic products for the primary purpose of inhibiting the development of micro-organisms in such products.
2. The substances marked with the symbol (*) may also be added to cosmetic products in concentrations other than those laid down in this Annex for other specific purposes apparent from the presentation of the product, e.g. as deodorants in soaps or as anti-dandruff agents in shampoo.
3. Other substances used in the formulation of cosmetic products may also have anti-microbial properties and thus help in the preservation of the products, as, for instance, may essential oils and some alcohols. These substances are not included in this Annex.
4. For the purposes of this list: "Salts" is taken to mean: salts of the cations sodium, potassium, calcium, magnesium, ammonium and ethanolamines: salts of the anions chloride, bromide, sulphate, acetate. "Esters" is taken to mean: esters of methyl, ethyl, propyl, isopropyl, butyl, isobutyl, phenyl.
5. All finished products containing formaldehyde or substances in this Annex and which release formaldehyde must be labelled with the warning "contains formaldehyde" where the concentration of formaldehyde in the finished product exceeds 0.05%.
NOTES
(1) Solely for products which might be used for children under three years of age and which remain in prolonged contact with the skin
(*) Concerns any products aimed to be applied on a large part of the body
(**) Solely for products, other than bath products/shower gels and shampoo, which might be used for children under three years of age
(***) Solely for products which might be used for children under three years of age

The invention claimed is:

1. A method for photokinetic intradermal delivery of a biologically active substance to a subject, the method comprising:
   (1) applying a formulation comprising the biologically active substance to a cellular surface on the skin of the subject; and,
   (2) illuminating said formulation on said cellular surface with a pulsed incoherent light having a selected wavelength, pulse rate and duty cycle, thus
   allowing said biologically active substance in said formulation to permeate said cellular surface, thereby effecting photokinetic intradermal delivery of the biologically active substance.

2. The method of claim 1, wherein the formulation comprises a gelling agent.

3. The method of claim 1, wherein the formulation further comprises a photocatalytic agent.

4. The method of claim 1, wherein said biologically active substance comprises sodium hyaluronate having a molecular weight (M.W.) of at least about 20 kDa, 50 kDa, 100 kDa, 200 kDa, 400 kDa, 500 kDa, 1000 kDa, 1250 kDa, 1500 kDa, 1600 kDa, 2000 kDa, 2100 kDa, 2200 kDa, 2500 kDa, 3000 kDa, 3500 kDa, 4000 kDa, 4500 kDa, or 5000 kDa; or hyaluronic acid (HA) having an average molecular weight (M.W.) of about 500 kDa, 600 kDa, 700 kDa, 800 kDa, 900 kDa, 1000 kDa, 1200 kDa, 1400 kDa, 1,600-2,200 kDa, or between 150-2180 kDa.

5. The method of claim 1, wherein said biologically active substance is a cosmetic agent, or a therapeutic agent.

6. The method of claim 1, wherein said biologically active substance comprises:
   (1) a peptide selected from the group consisting of Gly-Tyr, Val-TyrVal, Tyr-Gly-Gly-Phe-Met (SEQ ID NO: 1), Tyr-Gly-Gly-Phe-Leu (SEQ ID NO: 2), and Asp-Arg-Val-Tyr-Ile-His-Pro-Phe (SEQ ID NO: 3);
   (2) a hormone selected from the group consisting of methionine enkephalin acetate, leucine enkephalin, angiotensin II acetate, β-estradiol, methyl testosterone, and progesterone; or,
   (3) a protein selected from the group consisting of human growth hormones, insulin like growth factor-1 (IGF-1), enzymes, nonenzymes, antibodies, and glycoproteins.

7. The method of claim 1, wherein said pulsed incoherent light is selected from the group consisting of fluorescent, ultraviolet, visible, near infrared, LED (light emitting diode), and halogen light.

8. The method of claim 1, wherein said pulse rate is between about 1.7 cycles per second (cps) and about 120 cps, or about 1.7 cps and about 80 cps.

9. The method of claim 1, wherein said duty cycle is between about 1%ON99% OFF and about 99% ON1% OFF, or about 50%ON50% OFF and about 75%ON25% OFF.

10. The method of claim 1, wherein the biologically active substance has a molecular weight of no less than 10 kDa, 25 kDa, 50 kDa, 100 kDa, 150 kDa, 200 kDa, 250 kDa, 300 kDa, 350 kDa, 400 kDa, 500 kDa, 600 kDa, 700 kDa, 800 kDa, 900 kDa, 1,000 kDa, 1,500 kDa, 1,600 kDa, 2,000 kDa, 2,200 kDa, 2,500 kDa, or 3,000 kDa.

11. The method of claim 1, wherein the subject is human.

12. The method of claim 1, wherein the biologically active substance is dissolved in an aqueous solvent, or in an organic solvent.

13. The method of claim 1, wherein the biologically active substance is emulsified.

14. The method of claim 1, wherein the biologically active substance comprises an antioxidant.

15. The method of claim 1, wherein the biologically active substance comprises a vitamin.

16. The method of claim 15, wherein the vitamin is Vitamin E.

17. The method of claim 1, wherein the biologically active substance comprises a peptide.

18. The method of claim 1, wherein the biologically active substance comprises a skin component, an antioxidant or photoprotection molecule, Vitamin E, ascorbate, carotenoid, alpha-glycolic acid, SOD (Superoxide Dismutase), catalase, glutathione peroxydase, reductase, taurine, alpha-lipoic acid, polyphenol, mixture of resveratrol and epsilon-viniferin, mixture of polyphenolic, stilbene, falvonol, oligomer, polymer, melanin, glycerol, peptide, or a growth factor, glycoprotein, chondroitin sulphate, dermatan sulphate, cheratan sulphate, eparin, eparan sulphate, hyaluronate, decorin, collagene fiber, hydroxyproline (+Fe, +Vitamin C), hydroxylysine, glycine, tropocollagen, reticulin, keratin, elastin, matrix metallo-proteinase, beta-glucan, phytosterol, anti-aging molecule, Arginine, Citrulline, Ceramides, carnosine, Lysine, Inositol, Cysteine, squalene, squalane, chitin, sericine, theophylline-7 acetic acid, sodium ascorbyl phosphate, ascorbic acid, ascorbyl palmitate, pyridoxine, nicotinic acid, or lidocaine.

19. The method of claim 1, wherein said pulsed incoherent light is from a light emitting diode (LED).

20. The method of claim 1, wherein said pulsed incoherent light is visible light.

21. The method of claim 20, wherein said visible light is red light with a wavelength of about 700 nm.

22. The method of claim 1, wherein said pulsed incoherent light is infrared light.

23. The method of claim 22, wherein said infrared light has a wavelength of 830 nm or longer.

24. The method of claim 1, wherein said pulsed incoherent light has a wavelength range from about 340 nm to about 900 nm.

25. The method of claim 1, wherein said duty cycle is about 50% ON 50% OFF.

26. The method of claim 1, wherein said duty cycle is about 10% ON 90% OFF, or about 15% ON 85% OFF.

27. The method of claim 1, further comprises adjusting the flux rate of the biologically active substance by modulating the light energy, in order to deliver all or substantially all biologically active substance intradermally.

* * * * *